US012575825B2

(12) United States Patent
Bacchereti et al.

(10) Patent No.: US 12,575,825 B2
(45) Date of Patent: Mar. 17, 2026

(54) METHOD OF MANUFACTURING A GRIPPING SURFACE FOR AN END EFFECTOR AND SURGICAL INSTRUMENT COMPRISING A GRIPPING END EFFECTOR

(71) Applicant: MEDICAL MICROINSTRUMENTS, INC., Wilmington, DE (US)

(72) Inventors: Marco Bacchereti, Pisa (IT); Neri Pierotti, Pisa (IT); Giorgio Lazzari, Pisa (IT); Massimiliano Simi, Pisa (IT)

(73) Assignee: MEDICAL MICROINSTRUMENTS, INC., Wilmington, DE (US)

( * ) Notice: Subject to any disclaimer, the term of this patent is extended or adjusted under 35 U.S.C. 154(b) by 162 days.

(21) Appl. No.: 18/699,874

(22) PCT Filed: Oct. 12, 2022

(86) PCT No.: PCT/IB2022/059771
§ 371 (c)(1),
(2) Date: Apr. 9, 2024

(87) PCT Pub. No.: WO2023/062553
PCT Pub. Date: Apr. 20, 2023

(65) Prior Publication Data
US 2025/0235200 A1     Jul. 24, 2025

(30) Foreign Application Priority Data
Oct. 13, 2021     (IT) ........................ 102021000026186

(51) Int. Cl.
A61B 17/04       (2006.01)
A61B 17/06       (2006.01)
(Continued)

(52) U.S. Cl.
CPC .... A61B 17/0469 (2013.01); A61B 17/06066 (2013.01); A61B 17/06166 (2013.01); A61B 34/30 (2016.02); *A61B 2017/00429* (2013.01)

(58) Field of Classification Search
CPC .......... A61B 17/0469; A61B 17/06066; A61B 17/06166; A61B 17/00234; A61B 34/30;
(Continued)

(56) References Cited

U.S. PATENT DOCUMENTS

| | | |
|---|---|---|
| 7,331,967 B2 | 2/2008 | Woojin |
| 7,886,743 B2 | 2/2011 | Cooper |

(Continued)

FOREIGN PATENT DOCUMENTS

| | | |
|---|---|---|
| EP | 3362218 A1 | 8/2018 |
| EP | 3597340 A1 | 1/2020 |

(Continued)

OTHER PUBLICATIONS

International Search Report and Written Opinion received for PCT Serial No. PCT/IB2022/059771 on Jan. 18, 2023, 8 pgs.

*Primary Examiner* — Moshe Wilensky
(74) *Attorney, Agent, or Firm* — Merchant & Gould P.C.

(57) ABSTRACT

A manufacturing method by wire electro-erosion includes providing a wire electro-erosion machine having a cutting wire; mounting at least one workpiece to the wire electro-erosion machine; and making a surface micro-topography by wire electro-erosion. The method includes performing a first through cut on the workpiece according to a cutting path having peaks and valleys, thus exposing an exposed portion on the workpiece comprising reliefs and recesses corresponding to the peaks and valleys of the first cutting path. A surgical instrument includes at least one gripping surface having a surface micro-topography.

16 Claims, 23 Drawing Sheets

(51) Int. Cl.
  *A61B 34/30* (2016.01)
  *A61B 17/00* (2006.01)

(58) Field of Classification Search
  CPC .......... A61B 2017/00526; A61B 2017/00429;
  A61B 2017/00349; B23H 9/008; B23H
  7/02
  See application file for complete search history.

(56) References Cited

U.S. PATENT DOCUMENTS

| | | | |
|---|---|---|---|
| 7,947,050 B2 | 5/2011 | Lee |
| 8,004,229 B2 | 8/2011 | Nowlin |
| 8,005,571 B2 | 8/2011 | Sutherland |
| 8,123,740 B2 | 2/2012 | Madhani |
| 8,220,468 B2 | 7/2012 | Cooper |
| 8,281,670 B2 | 10/2012 | Larkin |
| 8,375,808 B2 | 2/2013 | Blumenkranz |
| 8,521,331 B2 | 8/2013 | Itkowitz |
| 8,540,748 B2 | 9/2013 | Murphy |
| 8,812,160 B2 | 8/2014 | Hagn |
| 8,831,782 B2 | 9/2014 | Itkowitz |
| 8,935,003 B2 | 1/2015 | Itkowitz |
| 8,939,963 B2 | 1/2015 | Rogers |
| 9,060,796 B2 | 6/2015 | Seo |
| 9,101,379 B2 | 8/2015 | Au |
| 9,408,668 B2 | 8/2016 | Durant |
| 9,554,866 B2 | 1/2017 | Cunningham |
| 9,629,680 B2 | 4/2017 | Winer |
| 9,743,989 B2 | 8/2017 | Itkowitz |
| 9,949,799 B2 | 4/2018 | Hingwe |
| 9,968,405 B2 | 5/2018 | Cooper |
| 10,123,844 B2 | 11/2018 | Nowlin |
| 10,219,870 B2 | 3/2019 | Mondry |
| 10,219,898 B2 | 3/2019 | Forsell |
| 10,292,661 B1 | 5/2019 | LaBorde |
| 10,299,873 B2 | 5/2019 | Hares |
| 10,307,199 B2 | 6/2019 | Farritor |
| 10,321,964 B2 | 6/2019 | Grover |
| 10,357,320 B2 | 7/2019 | Beira |
| 10,357,324 B2 | 7/2019 | Flatt |
| 10,376,323 B2 | 8/2019 | Farritor |
| 10,376,337 B2 | 8/2019 | Kilroy |
| 10,393,109 B2 | 8/2019 | Wu |
| 10,420,618 B2 | 9/2019 | Grover |
| 10,470,830 B2 | 11/2019 | Hill |
| 10,485,621 B2 | 11/2019 | Morrissette |
| 10,512,514 B2 | 12/2019 | Nowlin |
| 10,531,929 B2 | 1/2020 | Widenhouse |
| 10,561,468 B2 | 2/2020 | Cunningham |
| 10,624,708 B2 | 4/2020 | Hunter |
| 10,639,114 B2 | 5/2020 | Schuh |
| 10,653,489 B2 | 5/2020 | Kopp |
| 10,661,453 B2 | 5/2020 | Koenig |
| 10,736,706 B2 | 8/2020 | Scheib |
| 10,751,136 B2 | 8/2020 | Farritor |
| 10,758,298 B2 | 9/2020 | Felder |
| 10,779,898 B2 | 9/2020 | Hill |
| 10,789,329 B2 | 9/2020 | Lanting |
| 10,813,713 B2 | 10/2020 | Koch, Jr. |
| 10,820,953 B2 | 11/2020 | Kralicky |
| 10,881,477 B1 | 1/2021 | Genova |
| 10,888,390 B2 | 1/2021 | Higuchi |
| 10,898,281 B2 | 1/2021 | Cooper |
| 10,987,192 B2 | 4/2021 | Garcia Kilroy |
| 11,045,268 B2 | 6/2021 | Grover |
| 11,083,534 B2 | 8/2021 | Hares |
| 11,109,925 B2 | 9/2021 | Cooper |
| 11,172,997 B2 | 11/2021 | Kostrzewski |
| 11,179,209 B2 | 11/2021 | Kralicky |
| 11,179,211 B2 | 11/2021 | Zemlok |
| 11,246,670 B2 | 2/2022 | Swayze |
| 11,266,469 B2 | 3/2022 | Fuerst |
| 11,284,957 B2 | 3/2022 | Denlinger |
| 11,344,374 B2 | 5/2022 | Tekiela |
| 11,357,597 B2 | 6/2022 | Jhaveri |
| 11,406,465 B2 | 8/2022 | Zemlok |
| 11,417,928 B2 | 8/2022 | Cheng |
| 11,446,097 B2 | 9/2022 | Savall |
| 11,457,987 B2 | 10/2022 | He |
| 11,484,379 B2 | 11/2022 | Sutherland |
| 11,504,197 B1 | 11/2022 | Noonan |
| 11,504,203 B2 | 11/2022 | Flatt |
| 11,576,733 B2 | 2/2023 | Anglese |
| 11,607,279 B2 | 3/2023 | Chaplin |
| 11,666,401 B2 | 6/2023 | Denlinger |
| 11,684,434 B2 | 6/2023 | Shelton, IV |
| 2014/0005653 A1 | 1/2014 | Shelton, IV |
| 2017/0252112 A1 | 9/2017 | Crawford |
| 2017/0265949 A1 | 9/2017 | Crawford |
| 2020/0138534 A1 | 5/2020 | Garcia Kilroy |
| 2020/0197112 A1 | 6/2020 | Chin |
| 2020/0214779 A1 | 7/2020 | Masuda |
| 2020/0222134 A1 | 7/2020 | Schuh |
| 2020/0289223 A1 | 9/2020 | Denlinger |
| 2020/0330170 A1 | 10/2020 | Farritor |
| 2020/0397517 A1 | 12/2020 | Unsworth |
| 2020/0405408 A1 | 12/2020 | Shelton, IV |
| 2020/0405434 A1 | 12/2020 | Schuh |
| 2021/0052338 A1 | 2/2021 | Hill |
| 2021/0085301 A1 | 3/2021 | Au |
| 2021/0121260 A1 | 4/2021 | Genova |
| 2021/0153965 A1 | 5/2021 | Lau |
| 2021/0153966 A1 | 5/2021 | Lau |
| 2021/0196413 A1 | 7/2021 | Inoue |
| 2021/0197401 A1 | 7/2021 | Weintraub |
| 2021/0322119 A1 | 10/2021 | Hares |
| 2022/0031415 A1 | 2/2022 | Vargas |
| 2022/0047345 A1 | 2/2022 | Choi |
| 2022/0184823 A1 | 6/2022 | Bonny |
| 2022/0211452 A1 | 7/2022 | Clark |
| 2022/0218418 A1 | 7/2022 | Jolaeimoghaddam |
| 2022/0226056 A1 | 7/2022 | Beckman |
| 2022/0361736 A1 | 11/2022 | Danna |
| 2022/0370163 A1 | 11/2022 | Schuh |
| 2022/0378526 A1 | 12/2022 | Balicki |
| 2022/0378527 A1 | 12/2022 | Basafa |
| 2022/0378533 A1 | 12/2022 | McDiarmid |
| 2022/0395346 A1 | 12/2022 | Ihara |
| 2022/0401162 A1 | 12/2022 | Unsworth |
| 2023/0045591 A1 | 2/2023 | de la Fuente Klein |
| 2023/0149105 A1 | 5/2023 | Thornycroft |

FOREIGN PATENT DOCUMENTS

| | | |
|---|---|---|
| WO | 2003105705 A1 | 12/2003 |
| WO | 2005092551 A1 | 10/2005 |
| WO | 2017064305 A1 | 4/2017 |

100

101

1

102

44

1

42

29

METHOD OF MANUFACTURING A GRIPPING SURFACE FOR AN END EFFECTOR AND SURGICAL INSTRUMENT COMPRISING A GRIPPING END EFFECTOR

CROSS-REFERENCE TO RELATED APPLICATIONS

This application is the National Phase of International Application No. PCT/IB2022/059771, filed on Oct. 12, 2022, which claims the priority to Italian Patent Application No. 102021000026186, filed on Oct. 13, 2021, the entire contents of which are incorporated into this application by reference.

FIELD OF THE INVENTION

The present invention relates to a method of manufacturing one or more gripping surfaces with surface micro-topography for a surgical instrument.

The present invention further relates to a surgical instrument comprising one or more gripping surfaces with surface micro-topography.

PRIOR ART

Robotic surgery apparatuses are generally known in the art and typically comprise a central robotic tower (or cart) and one or more robotic arms extending from the central robotic tower. Each arm comprises a motorized positioning system (or manipulator) for moving a surgical instrument distally attachable thereto, in order to perform surgical procedures on a patient. The patient typically lies on an operating bed located in the operating room, in which sterility is ensured to avoid bacterial contamination due to non-sterile parts of the robotic apparatus.

Articulated surgical instruments for surgery or microsurgery typically comprise a pair of terminal links mutually articulated in opening/closing (grip), each having a free end for handling a needle as well as a suture thread for performing, for example, anastomosis procedures or other surgical or microsurgical therapies.

In order to handle needles and suture threads satisfactorily, offset ridges and valleys are generally made by molding on the gripping surfaces of the terminal links of the articulated surgical instrument so as to increase the gripping capacity on the surgical needle. Obviously, the dimensions of said offset ridges and valleys made by molding on the gripping surfaces determine the minimum manageable size of the needles and suture threads, which are generally thin elongated bodies.

The miniaturization of needles and suture threads is particularly desirable in robotic surgery or microsurgery because it allows reduced invasiveness for the patient and potentially faster recovery times.

Generally, a gripping surface having ridges and valleys made by molding is too coarse to handle a boosted miniaturization of the needle and suture thread, as well as of the surface itself, thus being ineffective at the micro-scale. Furthermore, molded micrometric elements could be highly fragile when in operation.

In particular, molding of ridges or sharp edges is extremely difficult as the scale decreases, as it becomes very complex to use cold molding techniques with very high hardness materials. The heat treatment that confers the hardness cannot be done after the finishing phase because the phase transformation of the material and the relative cooling can easily cause deformations of the material with consequent localized shrinkage and cracks, or even ruptures in the vicinity or in correspondence of the ridges and the sharp edges, which would therefore make the molding process highly unsatisfactory.

Some known solutions suggest to carry out treatments or finishes on the gripping surfaces of the surgical end effector by peeling (for example: shot peening, sandblasting) but even these techniques are not suitable for a boosted miniaturization of the pieces, i.e., they are unsuitable for making gripping surfaces of a miniaturized surgical end effector, due to the absence of control over the geometry of the resulting gripping surface which is intrinsic in this type of techniques.

For the purpose of miniaturizing the links of the articulated surgical instrument, as shown in WO-2017-064305, EP-3362218 and EP-3597340 to the same Applicant, articulated surgical instruments made by wire electro-erosion are known, which technique is also known as "WEDM", "wire-cut", "electro-erosion", "spark-machining", or "spark-eroding". This technology allows making through cuts on a cutting plane on one or more workpieces. By rotating the cutting equipment by 90° about an axis parallel to the longitudinal extension of the workpieces, it is possible to make a second through cut in a second cutting plane without repositioning the workpieces. Thereby, it is possible to shape a three-dimensional piece using a two-dimensional cutting technique. One of the two-dimensional through cuts creates the profile of the gripping surfaces. Therefore, the surfaces made on the workpiece with a wire electro-erosion cut are always parallel to the longitudinal direction of the cutting wire.

Further, the wire electro-erosion process of a metal, for example steel, is made by removing material from solid, and avoids altering the core (bulk) of the material. In fact, only a small, thin layer of the piece worked by electro-erosion is affected by structural alteration.

For example, the known document WO-03-105705 shows a microsurgical forceps made by wire electro-erosion starting from a single piece to be worked, in which to achieve the degree of freedom of opening/closing, a longitudinal gap is cut in the body of the single piece of the material to be worked, to separate the two parts ("jaws") of the forceps, making the body of each of said two parts of said forceps elastically flexible. The gripping surface of the forceps is shaped, i.e. is cut, from the cutting wire with a saw-tooth profile with a ridge extending transversely on the gripping surface which is particularly sharp.

Therefore, the need to improve the gripping capacity of a miniaturized surgical end effector is strongly felt, in order to be able to handle firmly and deftly a surgical needle and/or a miniaturized suture thread.

SUMMARY

It is an object of the present invention to obviate the drawbacks complained of with reference to the prior art.

According to an aspect of the invention, a surgical instrument comprises a functional surface having a surface micro-topography. The functional surface can be a gripping surface, adapted to grasp a micro-surgical needle and/or a miniaturized suture thread. The gripping surface can be intended to handle a slick and/or slippery tissue, as well as a tissue which is difficult to grasp, as well as a delicate tissue.

The functional surface can be a surface with increased friction for performing surgical or microsurgical procedures which do not necessarily carry out a gripping action under operating conditions, by way of a non-limiting example, stroke-end, abrasive, positioning condition, etc.

The surface micro-topography is preferably made by wire electro-erosion (WEDM).

According to an aspect of the invention, a surgical instrument comprises an end effector comprising at least two gripping surfaces facing each other and movable in a degree of freedom of opening/closing (grip), in which at least one gripping surface comprises a surface micro-topography.

The surface micro-topography is not necessarily made by means of a wire electro-erosion process, although preferably said surface micro-topography of said at least one gripping surface of the surgical instrument is made by wire electro-erosion.

The gripping surface comprising the surface micro-topography can be made in a single piece with a component of the end effector of the surgical instrument. For example, a gripping link of an end effector comprises said gripping surface made in a single piece with the body of the gripping link (it can be in a single piece with a termination element of a gripping link actuation tendon and/or with a junction element such as a hole or a pin of the gripping link).

The gripping surface comprising the surface micro-topography can be made in a separate piece with respect to the end effector and assembled thereto. For example, a gripping link of an end effector comprises in a single piece walls which form a fixing seat, and in which a component (such as a "pad", a plate, a block) comprising said surface micro-topography is fixed in said fixing seat (for example by gluing, interlocking, coupling, etc.). In such a case, the manufacturing method by wire electro-erosion makes a surface micro-topography on a gripping surface which will form a component to be fixed to a gripping link of an end effector of a surgical instrument. The fixing of the component can be releasable if required.

The surface micro-topography can belong to only one portion of the gripping surface. For example, the surface micro-topography can be made only on a longitudinal band of the gripping surface behind a free end of the end effector of the surgical instrument but which does not comprise such a free end. A first portion of the gripping surface with the surface micro-topography can be used to grasp a surgical or micro-surgical needle while a second portion can be used to grasp a suture thread, separately or concurrently with grasping said needle.

By virtue of the sizing and location of the portions with locally different features on the gripping surface, it is possible to adapt the manufacturing based on the tissue or the device which the gripping surface will have to grasp when in operating conditions. For example, a portion with sharp edges similar to an indentation and/or punching can be dedicated to grasping a surgical needle and/or a biological tissue which is difficult to grasp, while a flat portion of the same gripping surface can be dedicated to grasping suture threads or biological tissues which are not damaged.

Longitudinally, the gripping surface can comprise two or more portions with locally different features which make transverse bands with locally different features. The width of said transverse bands can be adjusted according to the clinical application for which the gripping surfaces are intended.

According to an aspect of the invention, there is provided a method of manufacturing at least one gripping surface of a surgical instrument by a wire electro-erosion process (WEDM) comprising the step of making at least one through cut on at least one workpiece according to a cutting path comprising peaks and valleys. Thereby, an exposed portion is created, comprising reliefs and recesses corresponding to said peaks and valleys of the cutting path.

By virtue of such a method it is possible to make a surface micro-topography by means of a through cut made with the cutting wire in which the reliefs and recesses of the micro-topography are parallel to the cutting wire and parallel to one another.

Making such a micro-topography with reliefs and recesses obtained with the cutting wire during cutting can result in an increase in the gripping capacity, making such a solution adapted to make gripping surfaces of a surgical instrument.

The diameter of the cutting wire can be chosen to adjust the pitch between adjacent reliefs of the micro-topography.

At least some of the recesses made by the through cut can be through cuts in a transverse direction of the micro-topography, making straight transverse through channels on the gripping surface having a substantially comparable gauge or slightly greater than the diameter of the cutting wire used to make the cut. The provision of transverse through channel cuts formed by said at least some of the recesses allows forming a transverse seat capable of receiving a surgical or micro-surgical needle as well as a suture thread.

According to an aspect of the invention, a surgical instrument comprises an end effector comprising at least two gripping surfaces facing each other and movable in a degree of freedom of opening/closing (grip), in which both gripping surfaces comprise a surface micro-topography in which the reliefs and recesses of the micro-topography are parallel to the cutting wire and are all parallel to one another.

The arrangement of the reliefs of a gripping surface can be chosen so that in closing conditions of the degree of freedom of opening/closing the reliefs of one gripping surface abut against the reliefs of the other gripping surface. The pitch between the reliefs can be adjusted so as to obtain a micro-topography with variable-pitch parallel reliefs.

The arrangement of the reliefs of a gripping surface can be chosen so that in closing conditions of the degree of freedom of opening/closing the reliefs of one gripping surface are offset with respect to the reliefs of the other gripping surface. The reliefs of one gripping surface can abut against side or bottom walls of the recesses of the other gripping surface. Thereby, it is possible to reduce the gauge of the straight transverse through channels of the gripping surface, making them adapted to firmly receive needles of a further reduced gauge.

The direction of the straight transverse channels is preferably transverse to the longitudinal extension direction of the gripping end elements comprising the gripping surfaces, for example tip links.

According to an aspect of the invention, there is provided a method of manufacturing at least one gripping surface of a surgical instrument by a wire electro-erosion (WEDM) process comprising the steps of: making at least a first through cut on at least one workpiece according to a first cutting path comprising peaks and valleys, then rotating the at least one workpiece, then performing a second through cut on the same exposed portion of the workpiece according to a second cutting path comprising peaks and valleys.

Due to the provision of two mutually rotated through cuts, a plurality of raised islands delimited by grooves is made, a micro-topography having a texture obtained from the union of the effects of the first and second cuts is made on said exposed portion. Thereby, the reliefs made by the first cut are interrupted by the recesses made by the second cut, thus forming raised islands. Meanwhile, the recesses made by the first cut can be in communication with the recesses made by the second cut, forming grooves delimiting the raised islands.

By virtue of such a method, the surface micro-topography made has straight transverse passage channels which in at least one definable transverse direction are narrower than the diameter of the cutting wire of the wire electro-erosion machine.

Thereby, it is possible to create gripping surfaces capable of grasping a surgical or micro-surgical needle of a further reduced gauge.

The two-dimensional cutting paths of the first and second cuts made by wire electro-erosion can be chosen to obtain the desired three-dimensional geometry of the gripping surface.

The rotation of the workpiece between the first and the second cut can be chosen to obtain the desired three-dimensional geometry of the gripping surface.

By adjusting the cutting parameters of the first and/or second cutting path, it is possible to adjust the gauge of the straight transverse channels of the gripping surface.

According to an aspect of the invention, a surgical instrument comprises an end effector comprising at least two facing gripping surfaces which are mutually movable in a degree of freedom of opening/closing (grip), in which both gripping surfaces comprise a surface micro-topography made by a wire electro-erosion process comprising the steps of: making at least a first cut through at least one workpiece according to a first cutting path comprising peaks and valleys, then rotating the at least one workpiece, then performing a second through cut on the same exposed portion of the workpiece according to a second cutting path comprising peaks and valleys.

The raised islands can each have a sharp free end. The grooves between the raised islands can have a curved and concave bottom, for example substantially an arc of a circle. By adjusting the cutting parameters of the first and/or second cutting path, it is possible to create, for example, groove bottoms all substantially at the same level, as well as raised islands which all extend in a cantilevered manner substantially at the same level.

The arrangement of the gripping surfaces can be chosen so that the raised islands of the first gripping surface are received in the grooves of the second gripping surface, and vice versa.

By virtue of the suggested solutions, it is possible to make a micro-topography on a gripping surface in a controlled and repeatable manner, by means of a manufacturing process by wire electro-erosion.

By virtue of the suggested solutions, it is possible to make a micro-topography on a gripping surface which makes the grip firmer and more precise, particularly on miniaturized elongated elements, such as needles and miniaturized suture threads.

It is thus possible to provide a surgical gripping tool with improved dexterity and capable of adapting to extreme miniaturization.

By virtue of the suggested solutions, it is possible to obtain one or more gripping surfaces having transverse micro-channels of a smaller gauge than the gauge of the cutting wire of the wire electro-erosion machine used for manufacturing.

By virtue of the suggested solutions, two gripping surfaces intended to be coupled when in operating conditions can be made, for example to exert a gripping action on a microsurgical needle as well as a miniaturized suture thread.

BRIEF DESCRIPTION OF THE DRAWINGS

Further features and advantages of the invention will become apparent from the following description of preferred embodiments thereof, given by way of a non-limiting example, with reference to the accompanying drawings which are briefly described below. It should be noted that references to "an" embodiment as well as to "an" operating mode in this disclosure do not necessarily refer to the same embodiment or operating mode, and are to be understood as at least one. Furthermore, for reasons of conciseness and reduction of the total number of drawings, a certain figure can be used to illustrate the features of more than one embodiment as well as more than one operating mode, and not all elements of the figure may be necessary for a certain embodiment or for a certain operating mode.

FIG. 1-B is an axonometric view of a surgical instrument, according to an embodiment.

FIG. 7-B shows a workpiece with an exposed portion obtained by the through cut in FIG. 7-A.

FIGS. 7-C and 7-D are axonometric views showing a tip link of a surgical instrument and a component or insert, respectively, each comprising a surface micro-topography obtained by the through cut in FIG. 7-A.

FIG. 8-B shows a workpiece with an exposed portion at the end of the second through cut in FIG. 8-A.

FIGS. 8-C and 8-D are axonometric views showing a tip link of a surgical instrument and a component or insert, respectively, each comprising a surface micro-topography at the end of the second through cut in FIG. 8-A.

FIG. 8-E is an axonometric view of a surface micro-topography comprising raised islands, according to an embodiment.

FIG. 10-C shows in separate parts a tip link, according to an embodiment, in which a component or insert comprises a surface micro-topography.

FIG. 15-B is a view of a gripping surface in FIG. 15-A according to a different point of view.

FIG. 15-C diagrammatically shows two gripping surfaces of a surgical instrument in a closing configuration, according to an embodiment, in which only one of the gripping surfaces comprises a surface micro-topography.

FIG. 25-B shows a block diagram of a method, according to a possible operating mode.

FIG. 25-C shows a block diagram of a method, according to a possible operating mode.

DETAILED DESCRIPTION

Figure 1A:
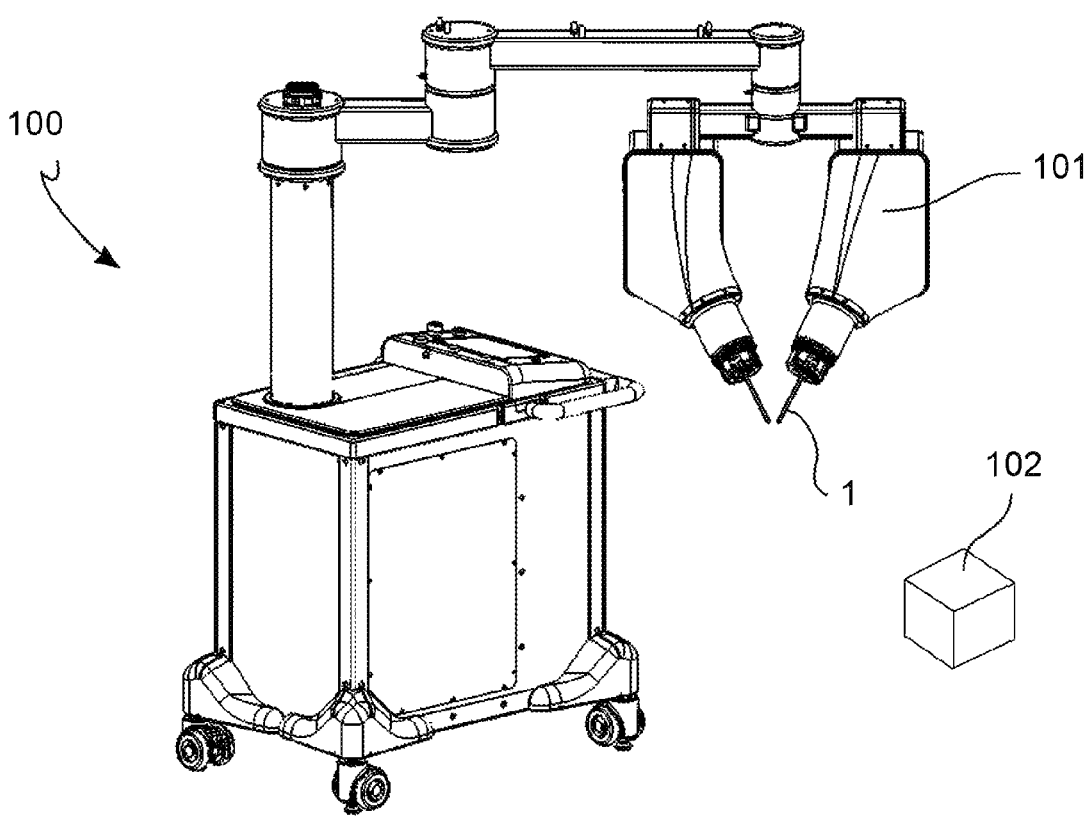
FIG. 1-A is an axonometric view of a robotic surgery system, according to an embodiment.
Figure 1B:
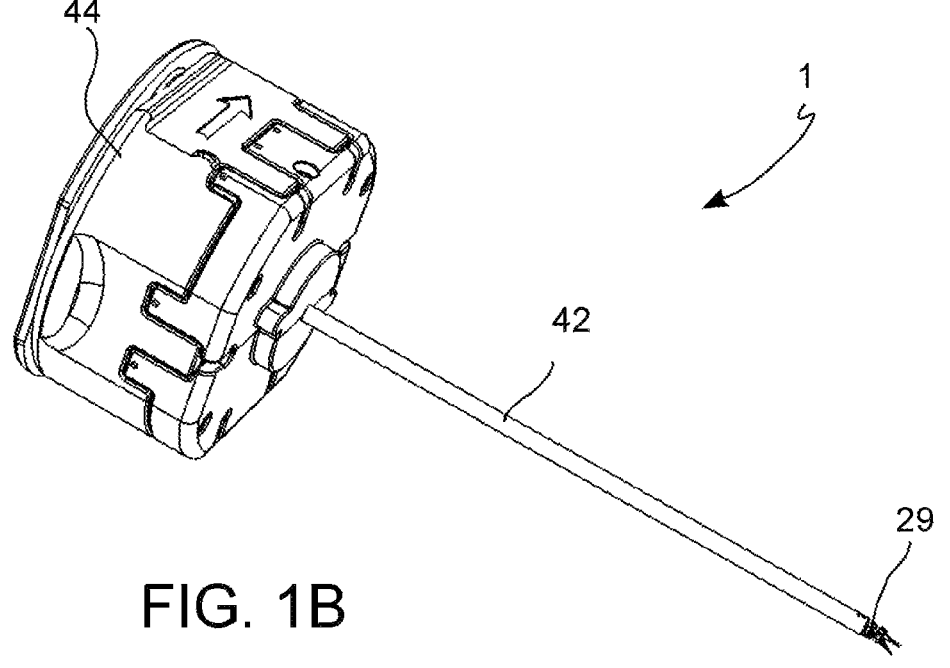

Reference throughout this description to "an embodiment" means that a particular feature, structure or function described in relation to the embodiment is included in at least one embodiment of the present invention. Therefore, the formulation "in an embodiment" in various parts of this description do not necessarily all refer to the same embodiment. Furthermore, particular features, structures or functions such as those shown in different drawings can be combined in any suitable manner in one or more embodiments. Similarly, reference throughout this description to "an operating mode" means that a particular feature, structure or function described in connection with the operating mode is included in at least one operating mode of the present invention. Therefore, the formulation "in an operating mode" in various parts of this description does not necessarily all refer to the same operating mode. Furthermore, particular features, structures or functions such as those shown in different drawings can be combined in any suitable manner in one or more operating modes.

In accordance with a general embodiment, there is provided a manufacturing method by wire electro-erosion ("wire-electro-discharge-machining", or "WEDM", or "spark erosion", according to the commonly adopted terminology).

The method comprises the step of providing a wire electro-erosion machine 2 comprising a cutting wire 3.

The cutting wire 3 preferably extends longitudinally between two heads 4, 5 of the wire electro-erosion machine 2 when in operating conditions. To perform the cut (i.e., electro-erosion), the cutting wire 3 advances along a cutting path in a feeding direction W (or cutting direction W) which is substantially orthogonal to the longitudinal extension of the cutting wire 3, i.e., the feeding direction is substantially orthogonal to the sliding direction of the stretch of the cutting wire 3 between the two heads 4, 5 of the machine 2, in a manner known per se. Each of the two heads 4, 5 can be associated with a reel 6 or winding/unwinding roller 6 for the cutting wire 3. When in operating conditions, the cutting wire 3 runs winding on one reel as it unwinds from the other reel, and the heads 4, 5 guide the cutting wire 3 in the feeding direction W (or cutting direction W) to perform a cut on the workpiece.

Figure 2:
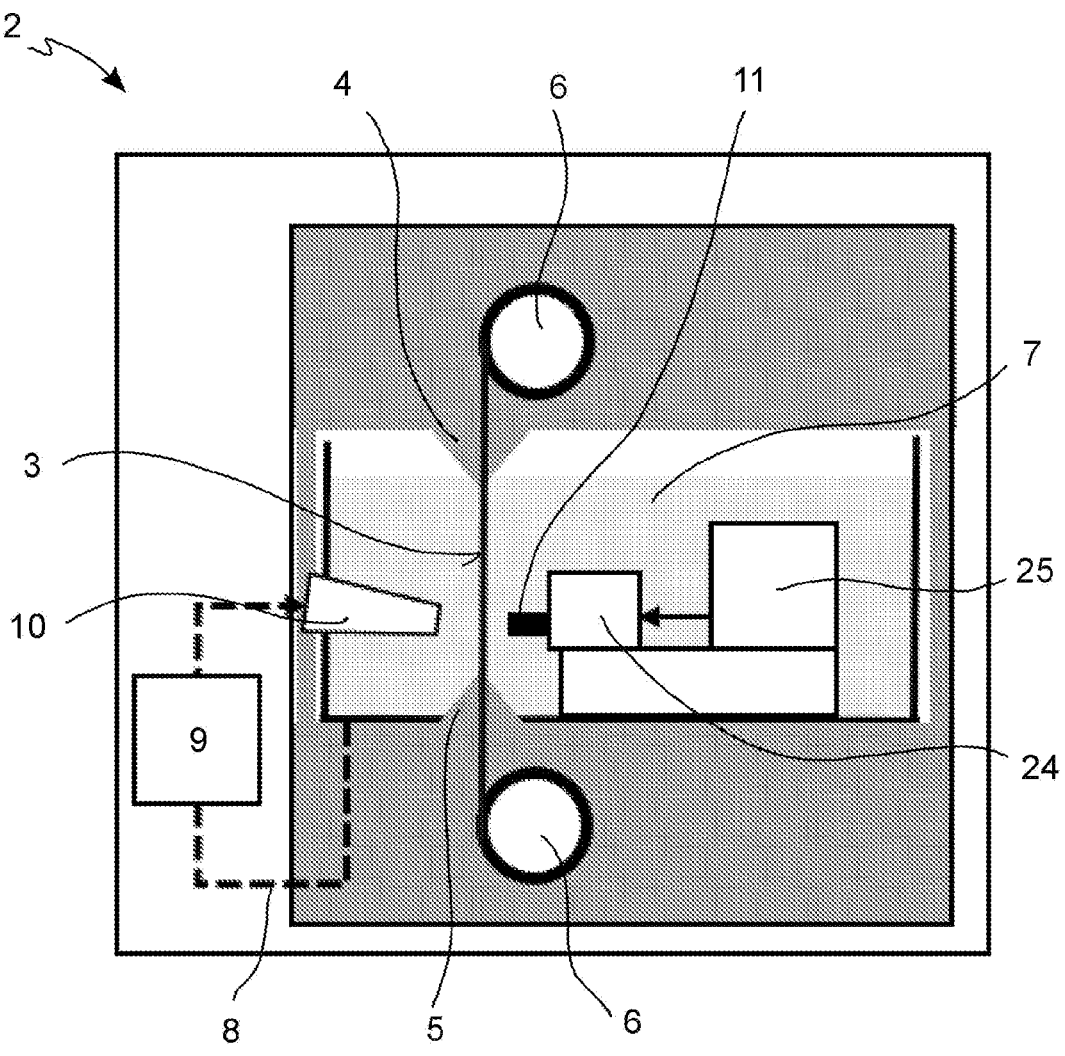
FIG. 2 diagrammatically shows a wire electro-erosion machine, according to an embodiment, in which a workpiece is mounted to the wire electro-erosion machine, according to a possible operating mode.
Figure 3A:
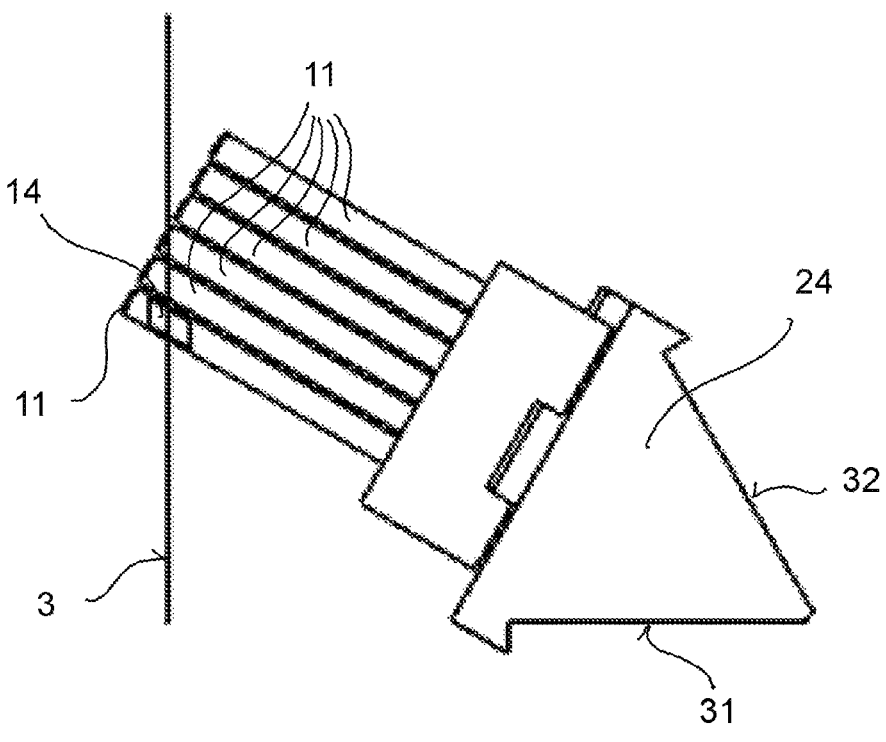
FIGS. 3-A, 3-B, 3-C and 3-D are vertical elevation, axonometry, axonometry views, respectively, according to another point of view and plan showing a support comprising a tooling for electro-erosion machine, according to an embodiment, in which a plurality of workpieces are mounted to the tooling, according to a possible operating mode.
Figure 3B:
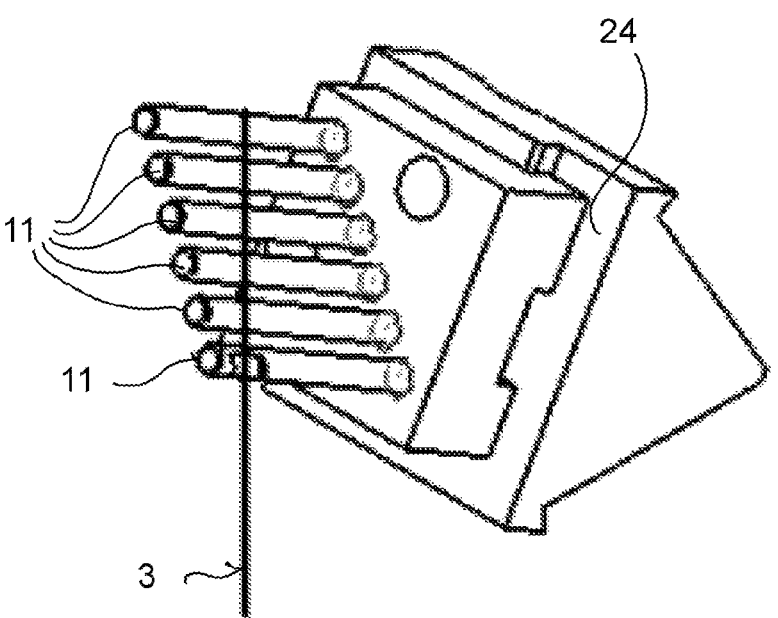
Figure 3C:
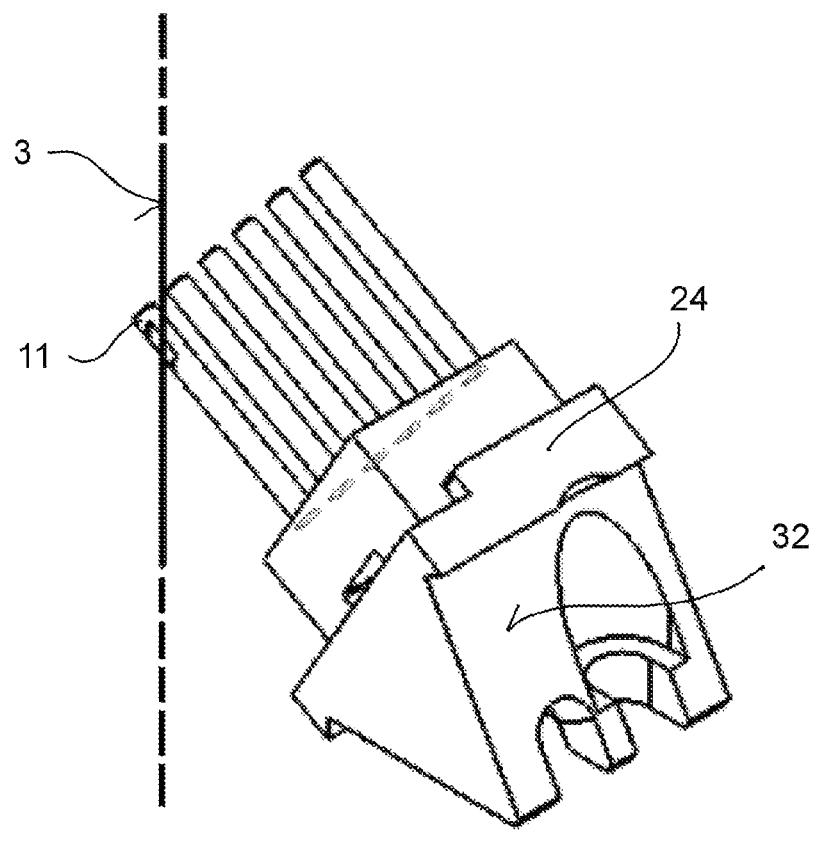
Figure 3D:
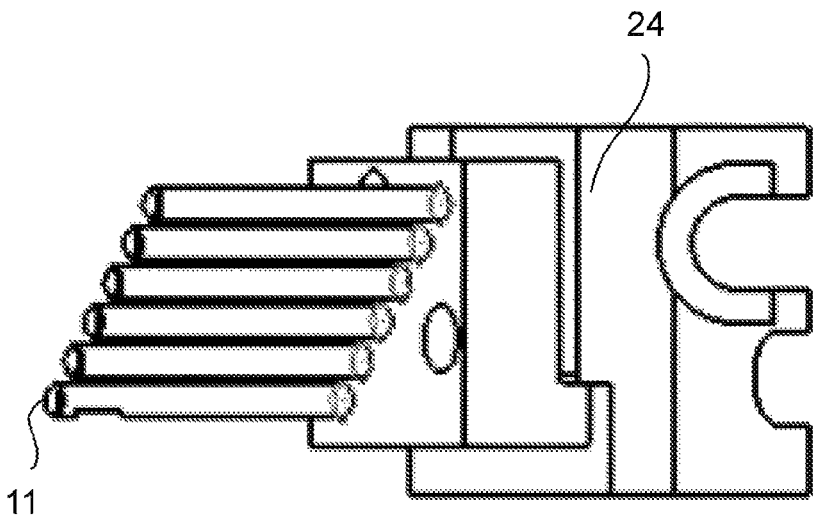

As shown for example in FIG. 2, the wire electro-erosion machine 2 preferably comprises a tank 7 to be filled with dielectric liquid inside which the electro-erosion of at least one workpiece occurs when in operating conditions. The electro-erosion machine 2 can further comprise a hydraulic circuit comprising a hydraulic duct 8 fitted with a pump 9 and a filter which withdraws and filters dielectric fluid from the tank 7 and ending with a nozzle 10 which directs dielectric fluid onto the workpiece.

The method further comprises the step of mounting at least one workpiece 11 to the wire electro-erosion machine 2.

The at least one workpiece 11 can have an elongated, e.g., cylindrical, body having a longitudinal axis X-X substantially coincident with the longitudinal extension direction of the workpiece 11.

The at least one workpiece 11 is preferably made of electrically conductive material, such as metal, or is coated with electrically conductive material.

Advantageously, the method further comprises the step of making a surface micro-topography on the at least one workpiece 11 by wire electro-erosion 2.

As diagrammatically shown in FIGS. 7-A and 7-B, the step of making a surface micro-topography comprises the step of performing a (first) through cut on the workpiece 11 according to a (first) cutting path 21 comprising peaks 12 and valleys 13. Said first through cut exposes on the workpiece 11 an exposed portion 14 on the workpiece 11. The exposed portion 14 comprises reliefs 15 and recesses 16 corresponding to said peaks 12 and valleys 13 of the first cutting path 21. In other words, since the first cutting path 21 comprises peaks 12 and valleys 13 it makes reliefs 15 and recesses 16 on the exposed portion 14 of the workpiece. For example, said reliefs 15 made by the cutting wire 3 can be ridges or cusps extending along a substantially straight direction and parallel to the cutting wire 3 during the first through cut. For example, said recesses 16 made by the cutting wire 3 can be open channels with a curved bottom which extend substantially straight and parallel to the ridges or cusps of said reliefs 15 and thus parallel to the cutting wire 3 during the first through cut.

In accordance with a possible operating mode, the step of mounting the workpiece 11 to the wire electro-erosion machine 2 comprises mounting the workpiece inclined with respect to the cutting wire 3. In other words, the longitudinal axis X-X of the workpiece 11 is pre-oriented so that it is neither parallel nor perpendicular to the cutting wire, as diagrammatically shown in FIG. 7-A. Thereby, the direction of the reliefs 15 and the recesses 16 (for example of the ridges and open channels) of the exposed portion 14 from the first through cut will be oriented neither parallel nor perpendicular to the longitudinal extension direction X-X of the workpiece 11, as shown for example in FIG. 7-B.

In accordance with a possible operating mode, the step of mounting the workpiece 11 to the wire electro-erosion machine 2 comprises mounting the workpiece parallel or orthogonal to the cutting wire 3. In other words, the longitudinal axis X-X of the workpiece 11 is oriented so that it is parallel or perpendicular to the cutting wire 3.

According to a preferred operating mode, after the step of making a first through cut, the method comprises the step of rotating the workpiece 11 with respect to the cutting wire 3 about a rotation axis R-R and, after the step of rotating, the method comprises the further step of making a second through cut having a second cutting path 22 comprising peaks 12 and valleys 13 on the same exposed portion 14 of the workpiece 11.

Preferably, said rotation axis R-R extends parallel to a direction exiting from the exposed portion 14 of the workpiece 11. Where the exposed portion 14 of the workpiece comprises reliefs 15 and recesses 16, the exiting direction is understood as a direction globally orthogonal to the exposed portion 14, and is not intended to indicate a direction locally orthogonal to an ascending (or descending) front of one of said reliefs 15. For example, where the exposed portion 14 of the workpiece 11 comprises recesses 16 in the form of open channels with curved bottom, then the exiting direction parallel to said rotation axis R-R is understood as the exiting direction from the bottom of said open channels of said recesses 16.

For example, as shown for example in FIG. 7-B, the direction exiting from the exposed portion 14 is understood as exiting from the sheet in that figure.

Preferably, said rotation axis R-R extends orthogonal to the extension of the cutting wire 3 and also orthogonal to the longitudinal extension direction X-X of the at least one workpiece 11.

In accordance with a possible operating mode, the rotating step is performed by rotating a support 24 associated with the at least one workpiece 11. In accordance with a possible operating mode, the rotating step is performed by a motor 25, which can be operatively connected to said support 24.

In accordance with an embodiment, as shown for example in FIG. 3-A, said support 24 comprises a manufacturing jig or tooling for a wire electro-erosion machine which is mounted to the wire electro-erosion machine 2. For example, said jig is a folding jig which is folded due to a rotation about said rotation axis R-R.

Figures 4, 5:
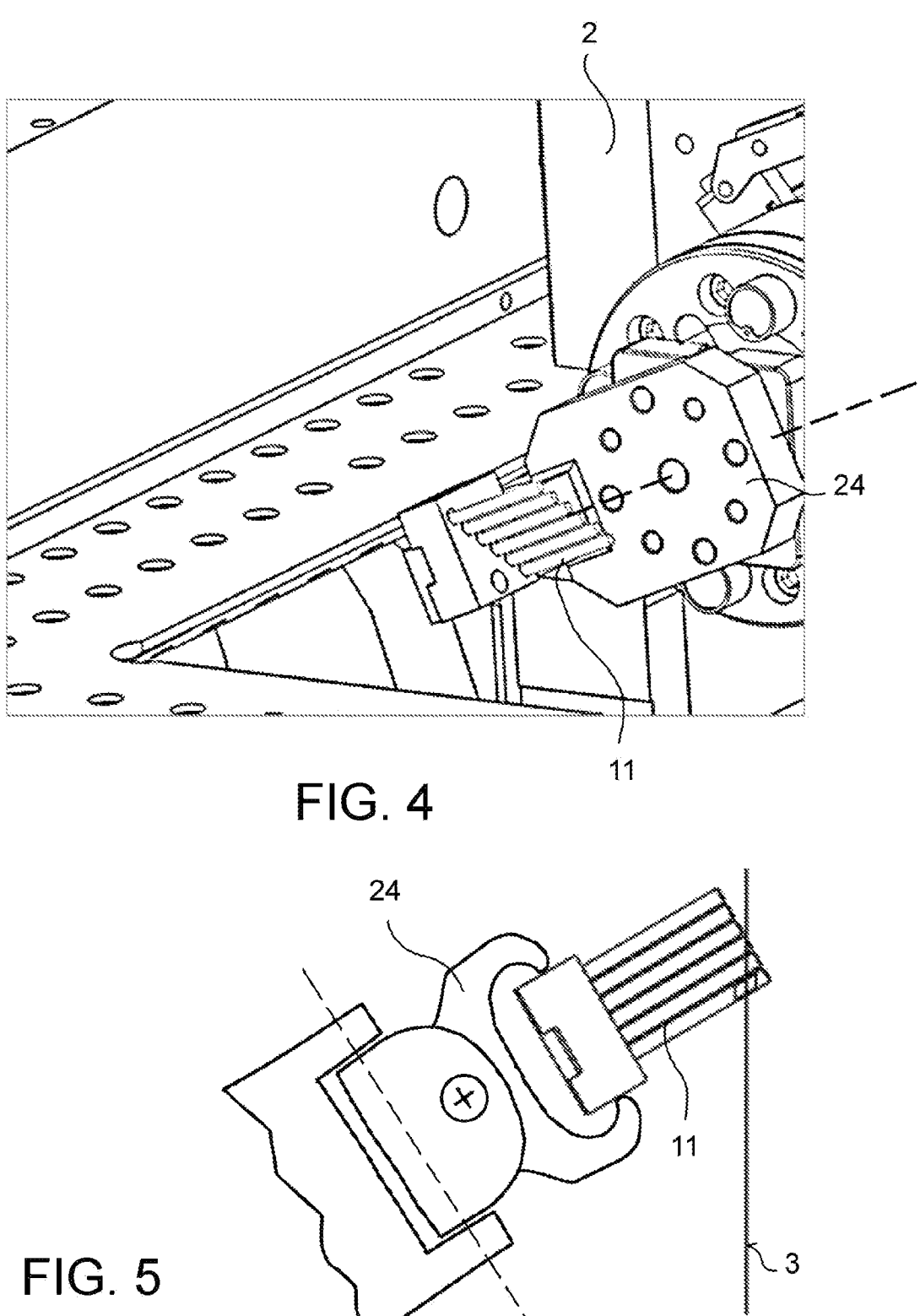
FIG. 4 is an axonometric view showing an electro-erosion machine provided with a rotary axis support, according to an embodiment, in which a plurality of workpieces are mounted to the tooling, according to a possible operating mode.
FIG. 5 is a diagrammatic view showing a support having a cooperative robotic arm, according to an embodiment, and a cutting wire, in which a plurality of workpieces are mounted to the tooling, according to a possible operating mode.

According to an embodiment, as shown for example in FIG. 4, said support 24 comprises a rotary axis of a wire electro-erosion machine 2. For example, said rotary axis is coincident with said rotation axis R-R. A further jig or tooling mounted downstream of the rotary axis can be provided.

In accordance with an embodiment, as shown for example in FIG. 5, said support 24 comprises an end effector of a robotic arm, for example a grip end effector of an anthropomorphic robotic arm. For example, said rotation axis R-R can coincide with an articulation axis of the anthropomorphic robotic arm and/or with a rotation axis of a definable control point rigidly associated with the robotic arm forming the support 24.

By virtue of such a method, it is possible to make a surface micro-topography 20 having a plurality of raised islands 17 delimited by grooves 18 on said exposed portion 14 of the workpiece 11. Preferably, said grooves 18 entirely delimit said raised islands 17. Said surface micro-topography 20 therefore results in a micro-texturing made by a wire electro-erosion process.

Each of said two non-parallel and mutually inclined through cuts of an angle α on the same exposed portion 14 of the workpiece 11 makes a plurality of substantially straight reliefs and recesses on the workpiece, and the combination or crossing of the reliefs and recesses of the two through cuts makes said plurality of raised islands 17 delimited by grooves 18, thus forming said surface micro-topography 20. For example, the grooves 18 will originate from the union of said recesses 16 made by the first and second through cuts.

In accordance with an embodiment, the raised islands 17 of the surface micro-topography 20 are substantially protrusions projecting cantilevered from the level of the grooves 18 in a direction parallel to the rotation axis R-R.

By virtue of such a method, the surface micro-topography 20 has straight transverse passage channels 19 which are narrower, in at least one definable direction transverse to the longitudinal direction X-X of the workpiece 11, than the gauge of the cutting wire 3 of the wire electro-erosion machine 2. By virtue of such a method, it is thus possible to make by wire electro-erosion a gripping surface 23 for a surgical instrument 1 having a surface micro-topography 20 which has narrower straight transverse passage channels 19 than the gauge of the cutting wire 3, and adapted to firmly grasp elongated elements to be grasped (such as suture needles and/or suture threads) which have a smaller gauge than the gauge of the cutting wire 3.

This promotes an extreme miniaturization of the micro-texturing of the surface micro-topography 20 made with such a manufacturing method by wire electro-erosion.

The gauge of the straight transverse passage channels 19 can be adjusted by the choice of the rotation angle α about the rotation axis R-R as well as the choice of the pitch between two adjacent peaks 12 of the first or second cutting path 21, 22.

In accordance with a possible operating mode, the rotation angle α is in the range of 30° to 120°, i.e., in other words, the rotating step comprises rotating the workpiece 11 by a rotation angle α with respect to the cutting wire 3 between 30° and 120°. In accordance with a possible operating mode, the rotation angle α is greater than 45°, and for example is between 45° and 120°. In accordance with a possible operating mode, the rotation angle α is greater than or equal to 60°.

The straight transverse direction of the straight transverse passage channels 19 made on the surface micro-topography 20 is not parallel to the directions of the first and second through cuts performed by the cutting wire 3.

In accordance with a preferred embodiment, the direction of the straight channels 19 is orthogonal to the longitudinal axis X-X of the workpiece 11. In accordance with an embodiment, the direction of the straight transverse channels 19 is inclined with respect to the longitudinal axis X-X of the workpiece 11, while avoiding being orthogonal to the longitudinal axis X-X.

The direction of the straight transverse channels 19 can be adjusted by acting on the cutting parameters such as the rotation angle of the workpiece 11 with respect to the cutting wire and/or the initial positioning angle of the workpiece 11 with respect to the cutting wire and/or the pitch between two adjacent peaks 12 of the cutting paths 21, 22.

Figures 11A, 11B, 12A, 12B:
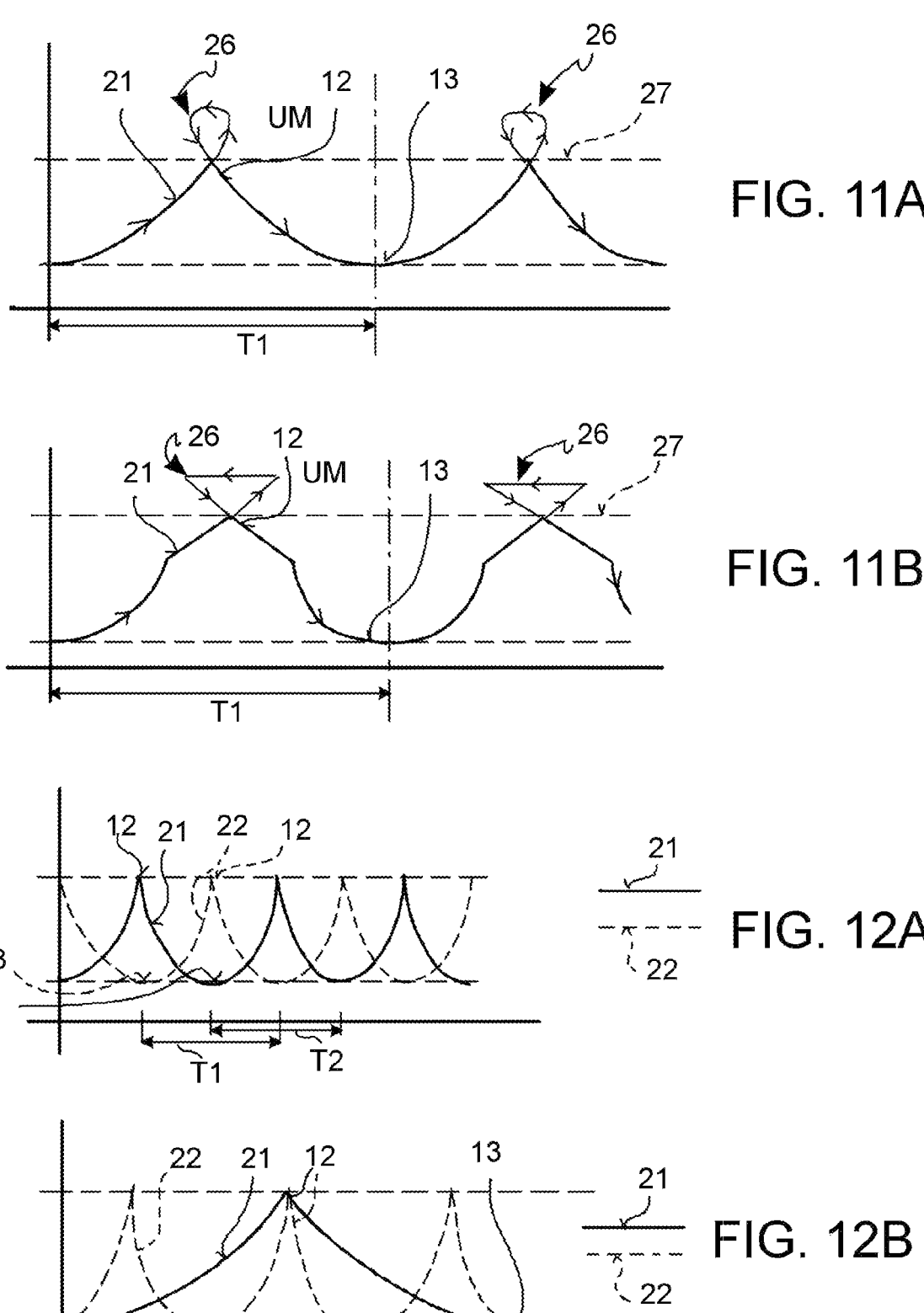
FIGS. 11-A and 11-B are graphs showing a section of a cutting path, according to a possible operating mode.
FIGS. 12-A and 12-B are graphs comparing a section of a first cutting path of a first through cut with a portion of a second cutting path of a second through cut, according to a possible operating mode.
Figures 13A, 13B, 13C:
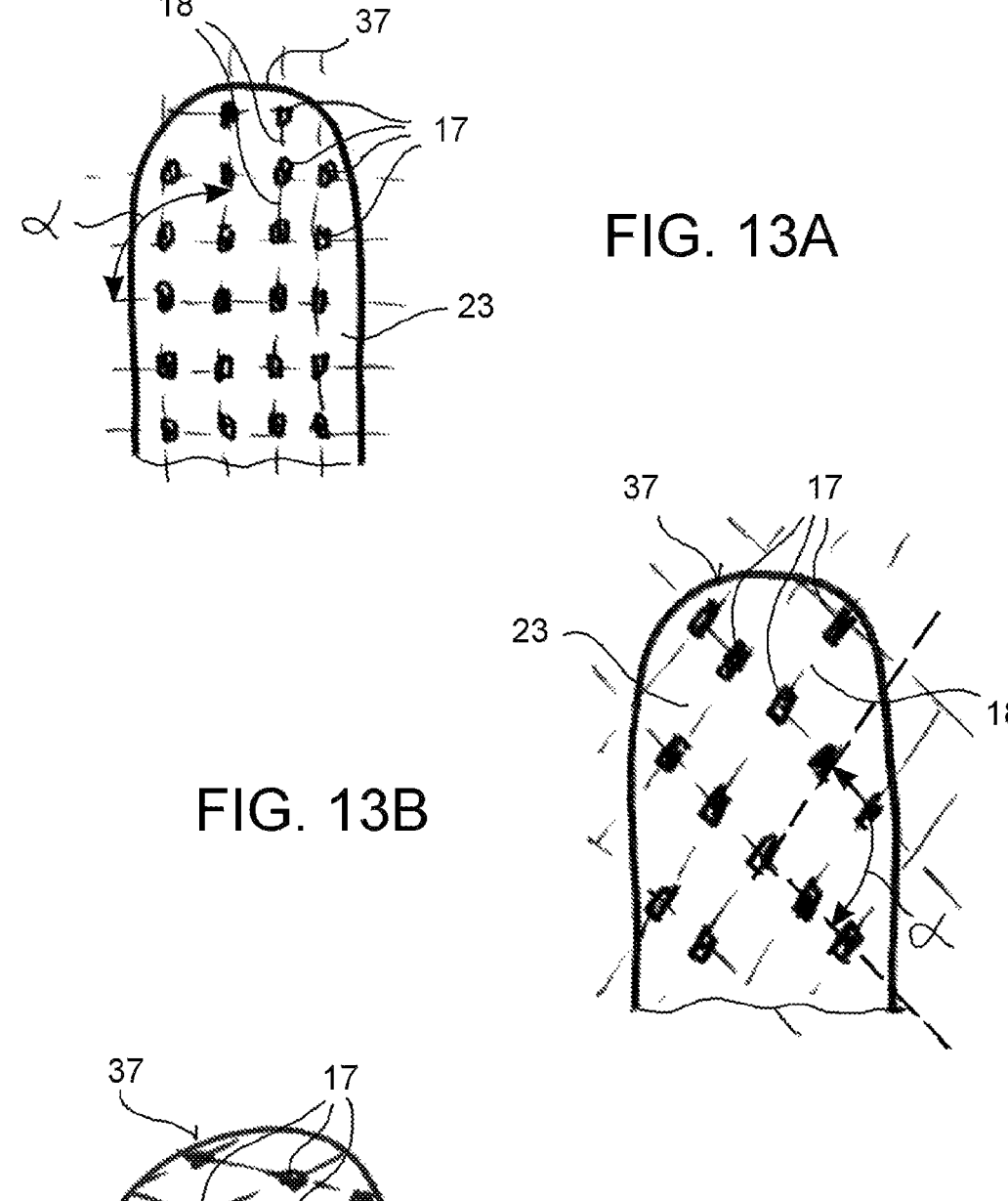
FIGS. 13-A, 13-B and 13-C are diagrammatic views of a gripping surface of a surgical instrument, according to some embodiments.

In accordance with an embodiment, the first cutting path 21 comprises a path modular unit UM including at least one peak 12 and at least one valley 13, in which said path modular unit UM repeats equal thereto with a first periodicity T1 or first step T1, as shown for example in FIGS. 11-A and 11-B. The first periodicity T1 can be fixed or variable. For example, the first periodicity T1 can be evaluated as the spatial or temporal distance between two adjacent peaks 12 of the cutting path 21. The path modular unit UM can comprise more than one peak 12. The same features and properties described with reference to the first modular unit UM of the first cut 21 can be applied to the second modular unit UM of the second cutting path 22 having a second periodicity T2 thereof. The first modular unit UM of the first cutting path 21 can be the same or different from the second modular unit UM of the second cutting path 22.

As shown for example in FIG. 12-A, in accordance with an embodiment, the second cutting path 22 comprises a second path modular unit UM which is equal to the first path modular unit UM of the first cutting path 21 and offset with respect thereto.

As shown for example in FIG. 12-B, in accordance with an embodiment, the first cutting path 21 comprises a first path modular unit UM having three times the periodicity T1 with respect to the modular unit UM of the second cutting path 22. In other words, the first periodicity T1 in such a figure is substantially equal to three times the second periodicity T2.

The periodicity can be obtained by choosing the gauge of the cutting wire 3. For example, two different cutting wires differing from each other in the gauge can be used, in which a first cutting wire is used to make the first through cut along the first cutting path 21 and the second cutting wire is used to make the second through cut along the second cutting path 22.

At least one cutting path 21, 22, and preferably both, can comprise a plurality of cusps.

In order to describe peaks 12 adapted to generate sharp reliefs 15, the cutting path 21 or 22 can describe an extra ring-shaped path 26 outside the workpiece 11. In other words, to make sharp reliefs 15 and thus to make a non-continuous broken path having narrow steering/breaking angles, the cutting path 21 or 22 can extend beyond the level 27 (e.g., corresponding to an outer edge of the workpiece 11 and/or to an outer edge of the surface micro-topography 20 to be obtained), as shown for example in FIGS. 11-A and 11-B.

In accordance with a preferred embodiment, at least some islands and preferably all the islands of said plurality of raised islands 17 made on the surface micro-topography 20 comprise a sharp free end 28.

In accordance with an embodiment, at least some islands and preferably all the islands of said plurality of raised islands 17 made on the surface micro-topography 20 have substantially pyramidal geometry extending from the level of the grooves 18. For example, the pyramidal geometry has a quadrangular base (e.g., parallelogram, square, rectangle) at the level of the grooves. The side walls of such a pyramidal geometry of the raised islands 17 can be curved and concave or they can be flat, inclined with respect to the exiting direction (and thus to the rotation axis R-R) and substantially triangular in shape.

In accordance with a possible operating mode, the method comprises the step of making a surface micro-topography 20 further comprises the further step of flattening, or making a flattening, at least locally on the workpiece 11, exposing a flattened surface to be worked which will be subject to said first cut 21. For example, the flattening step can comprise removing material from the workpiece 11. The workpiece 11 can have a cylindrical body and the flattening step can comprise flattening a portion of a cylindrical surface of the cylindrical body of the workpiece 11, making a substantially flat surface parallel to the longitudinal extension axis X-X of the workpiece 11. In other words, in accordance with a possible operating mode, the method comprises the further step of making an initial roughening, i.e., an at least partial flattening, on the workpiece 11 exposing a flat surface to be worked on the substantially flat workpiece 11. This step of making an initial roughening can be performed before the step of making a surface micro-topography. This step of making an initial roughening can belong to the step of making a surface micro-topography and can be performed by the cutting wire 3 of the wire electro-erosion machine 2.

This step of making an initial roughening can be performed before the step of mounting the at least one workpiece 11 to the wire electro-erosion machine 2. For example, the workpiece 11 can comprise one or more gaps each having a flat surface to be worked.

The step of making a surface micro-topography 20 can make a surface micro-topography on a portion of said flat surface to be worked and/or on the entirety thereof.

In accordance with an embodiment, at least some and preferably all the grooves 18 between the raised islands 17 have a curved and concave bottom. Preferably, the concave bottom is substantially circular i.e., has a profile substantially describing an arc of circumference.

The level of the grooves 18, i.e., the level of the bottom of the grooves 18 can be substantially the same for all the grooves 18 of the surface micro-topography 20. This can be achieved by implementing said first and second cutting paths 21, 22 having valleys 13 all at the same level, which make through cuts at the same depth on the workpiece 11.

The level of the free end 28 of the raised islands 17 can be the same for all the raised islands 17 of said plurality. This can be achieved by implementing said first and second cutting paths 21, 22 having peaks 12 all at the same level, which make through cuts at the same depth on the workpiece 11.

The extent in the protrusion direction of the raised islands 17 can be substantially the same for all the raised islands 17 of said plurality.

In accordance with a possible operating mode, a plurality of surface micro-topographies 20 can be made on said at least one workpiece 11.

Figure 14:
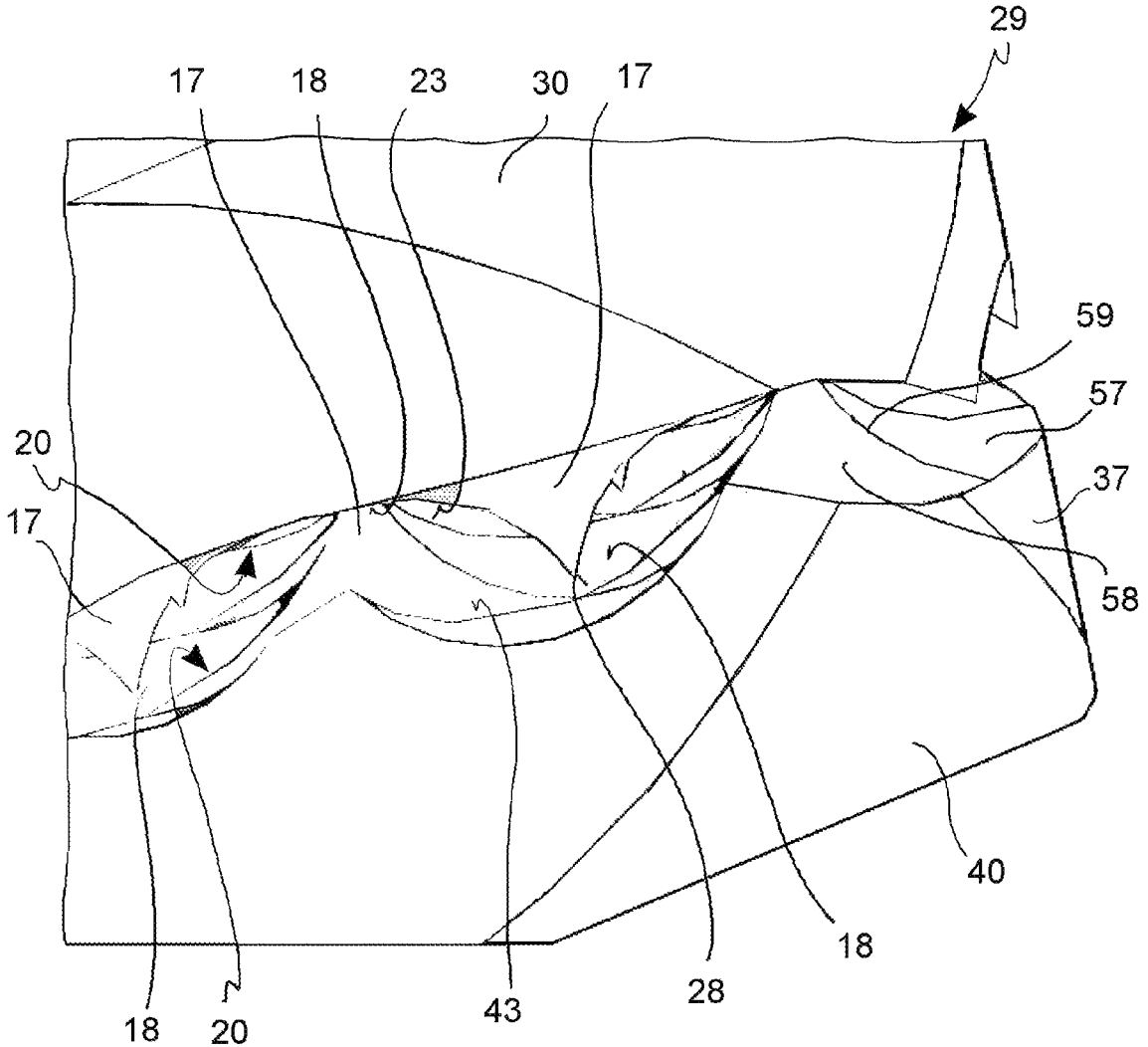
FIG. 14 is an axonometric view showing two gripping surfaces of a surgical instrument in a closing configuration, according to an embodiment.

In accordance with a possible operating mode, two surface micro-topographies 20 of said plurality are intended to be facing when in operating conditions, i.e., when they form gripping surfaces 23,43 facing each other and intended to exert jointly a gripping action, for example on a surgical needle and/or on a suture thread, and for example belong to respective gripping links 30, 40. In such a case, in accordance with an embodiment, the arrangement of the raised islands 17 of one gripping surface 23 is offset with respect to the arrangement of the raised islands 17 of the other gripping surface 43, so that when the gripping surfaces 23, 43 are closed in a closed configuration the raised islands 17 of one gripping surface 23 are inserted into the grooves 18 of the other gripping surface 23, and vice versa, as shown for example in FIG. 14. For example, the free ends 28 of the raised islands 17 of one gripping surface 23 can abut against the bottom walls of the grooves 18 of the other facing gripping surface. Thereby, with a closed surgical instrument, it is possible to create straight transverse passage channels 19 of a further reduced gauge.

Figure 6:
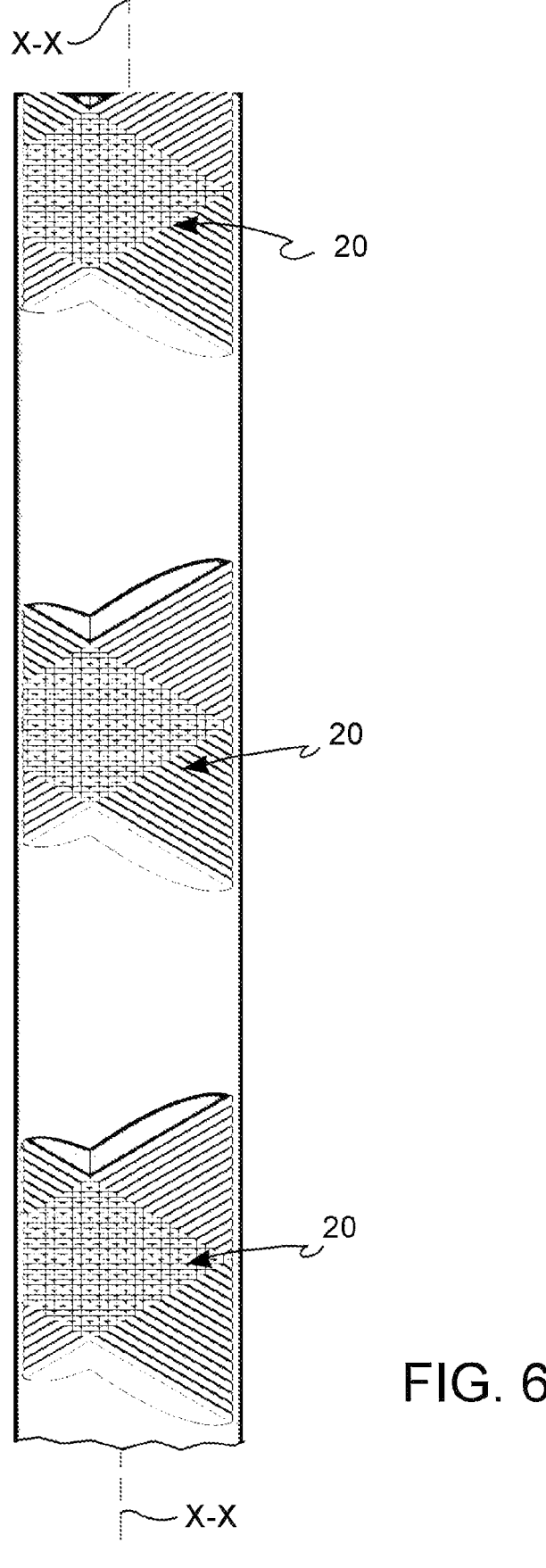
FIG. 6 shows a workpiece comprising a plurality of surface micro-topographies, according to a possible operating mode.
Figure 7A:
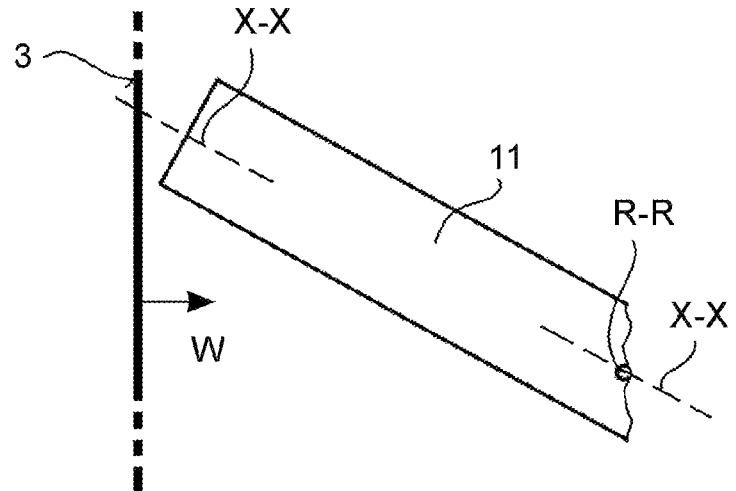
FIG. 7-A is a diagram which diagrammatically shows a step of performing a through cut, according to a possible operating mode.
Figure 7B:
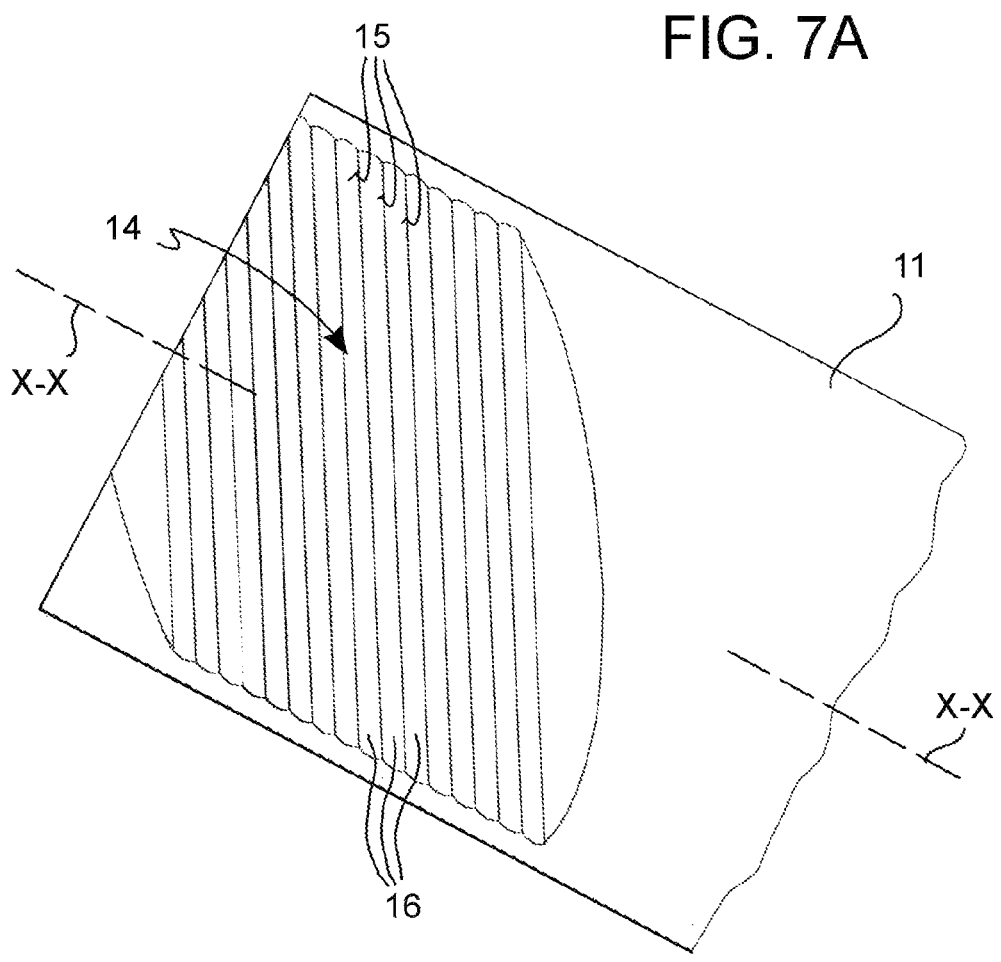
Figure 7C:
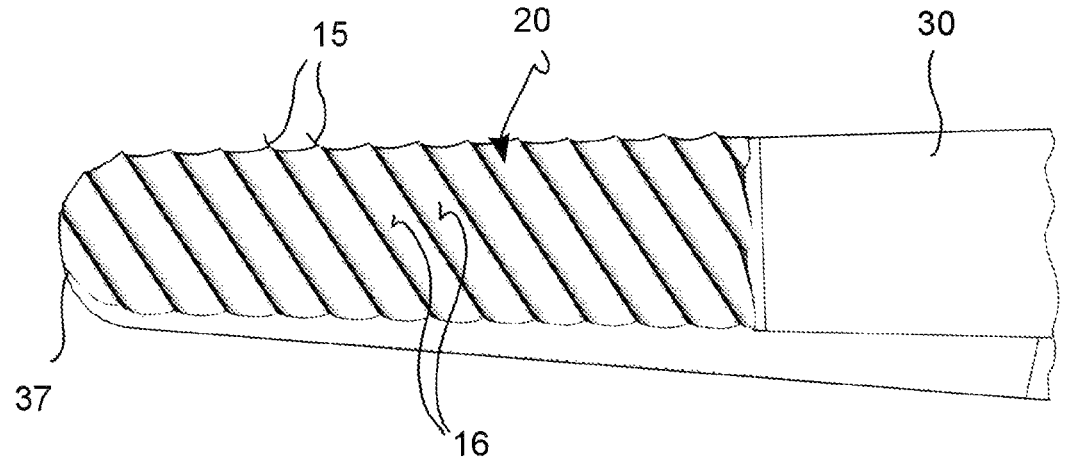
Figure 7D:
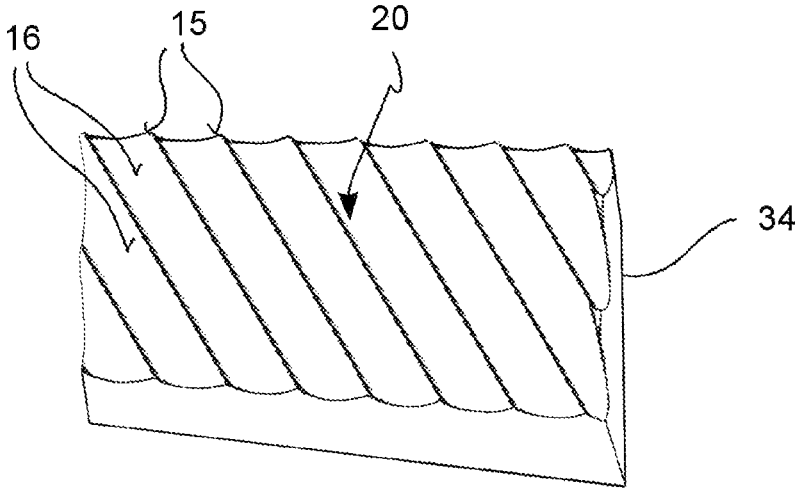
Figure 8A:
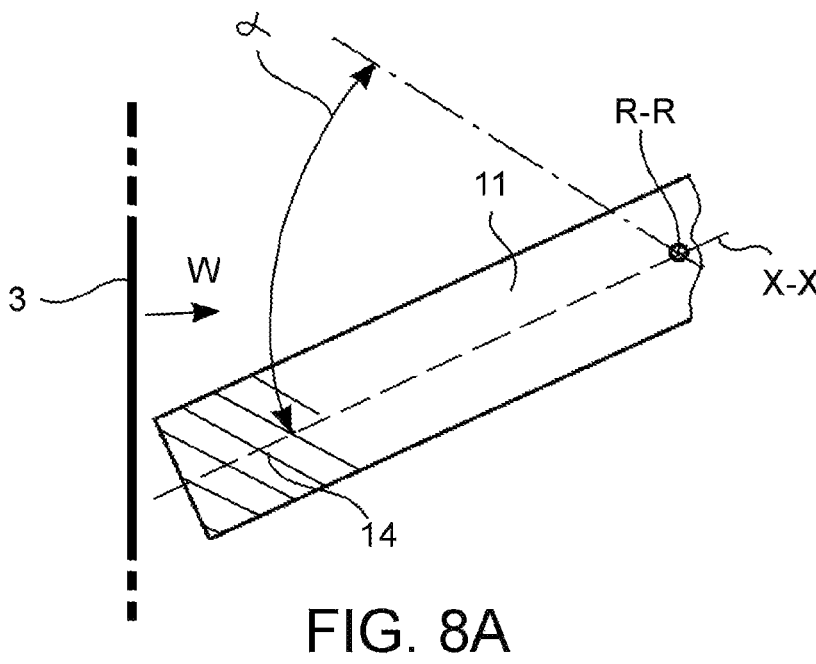
FIG. 8-A is a diagram which diagrammatically shows a step of performing a second through cut, according to a possible operating mode.
Figure 8B:
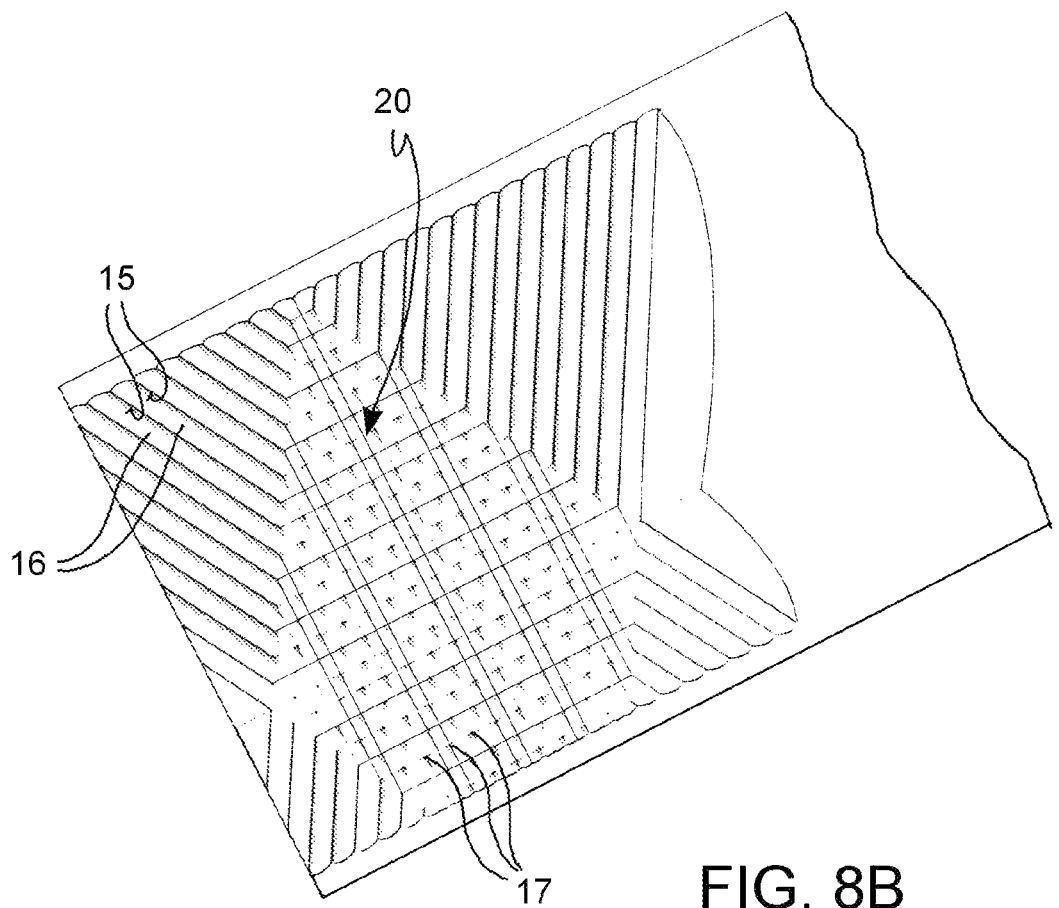
Figure 8C:
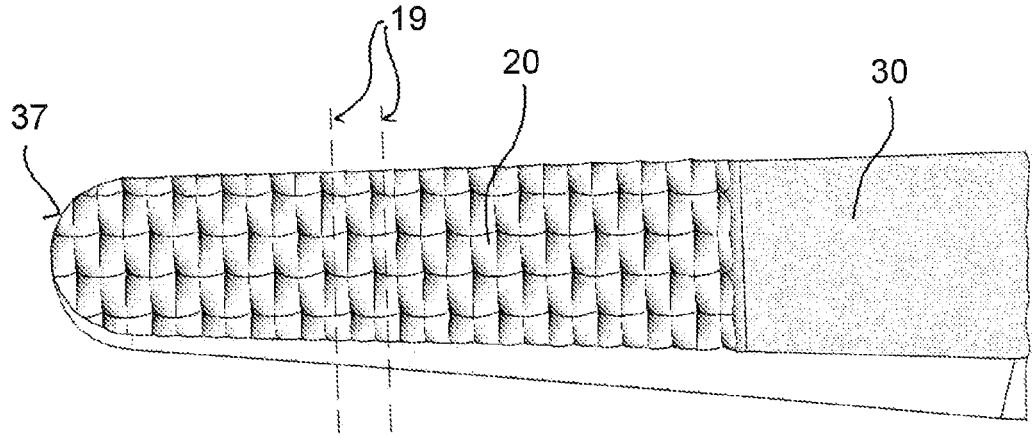
Figure 8D:
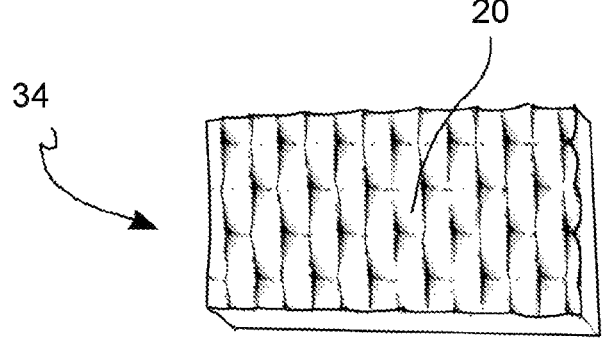
Figure 8E:
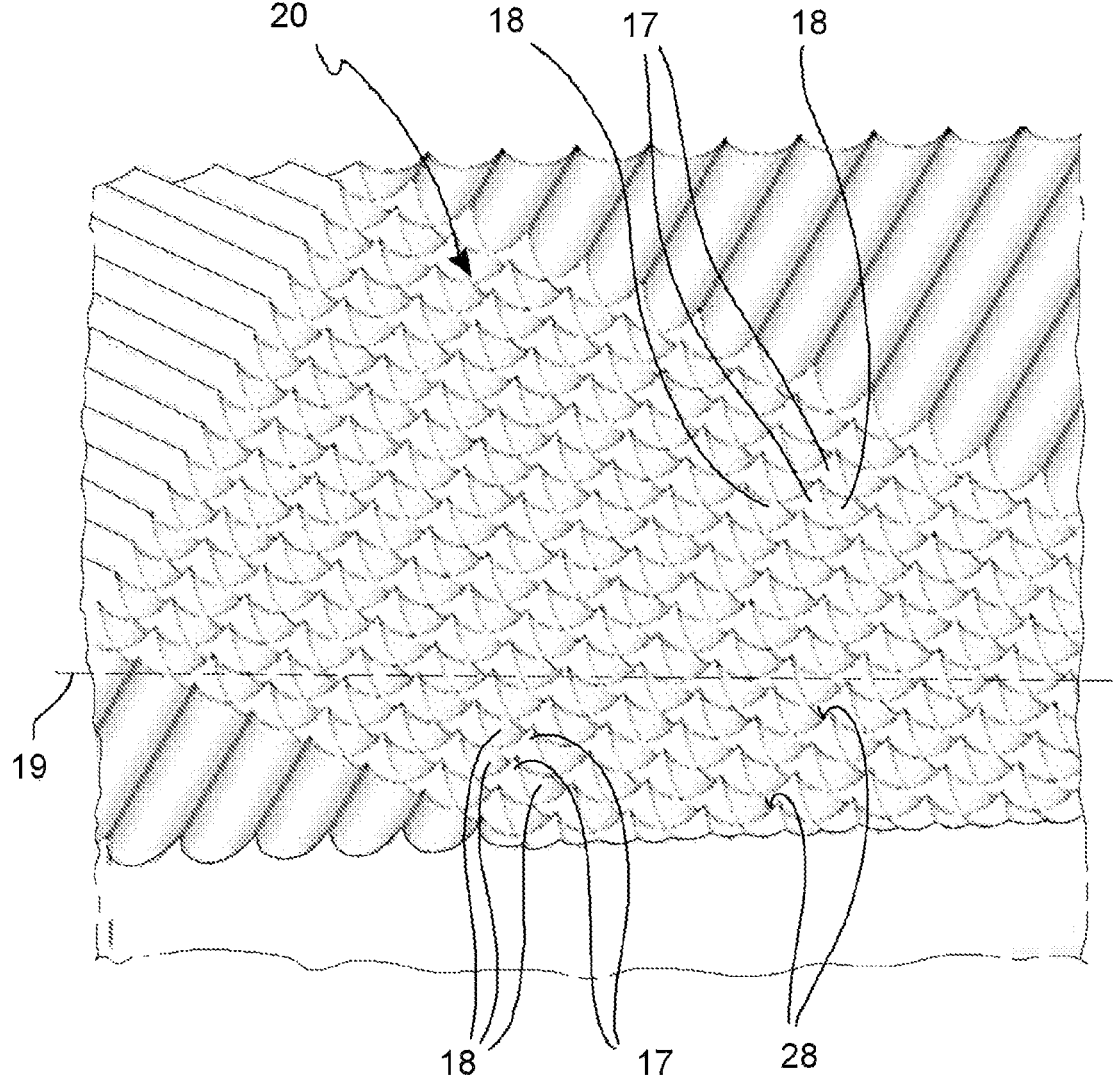

In accordance with a possible operating mode, as shown for example in FIG. 6, a single workpiece 11 comprises a plurality of surface micro-topographies 20. For example, the surface micro-topographies of said plurality are spaced longitudinally along the single workpiece 11.

In accordance with a possible operating mode, there is provided a plurality of workpieces 11 comprising said at least one workpiece 11.

In accordance with a possible operating mode, there is provided a plurality of workpieces 11 comprising said at least one workpiece, in which the workpieces 11 of said plurality are mounted to the support 24 and arranged so that the cutting wire 3 intersects at most one workpiece 11 of said plurality at a time on at least one cutting plane. Preferably, the workpieces 11 of said plurality are mounted to the support 24 and arranged so that the cutting wire 3 intersects at most one workpiece 11 of said plurality at a time on at least two cutting planes. In accordance with an embodiment, the workpieces 11 of said plurality are mounted to the support 24 and arranged so that the cutting wire 3 intersects at most one workpiece 11 of said plurality at a time on at least three cutting planes.

In accordance with a possible operating mode, a plurality of surface micro-topographies 20 are made on the same workpiece 11, which for example follow one another along the longitudinal extension of the workpiece 11 and which can form a respective plurality of gripping surfaces 23.

In accordance with a possible operating mode, the method further comprises the further step of shaping the at least one workpiece 11.

Figure 9:
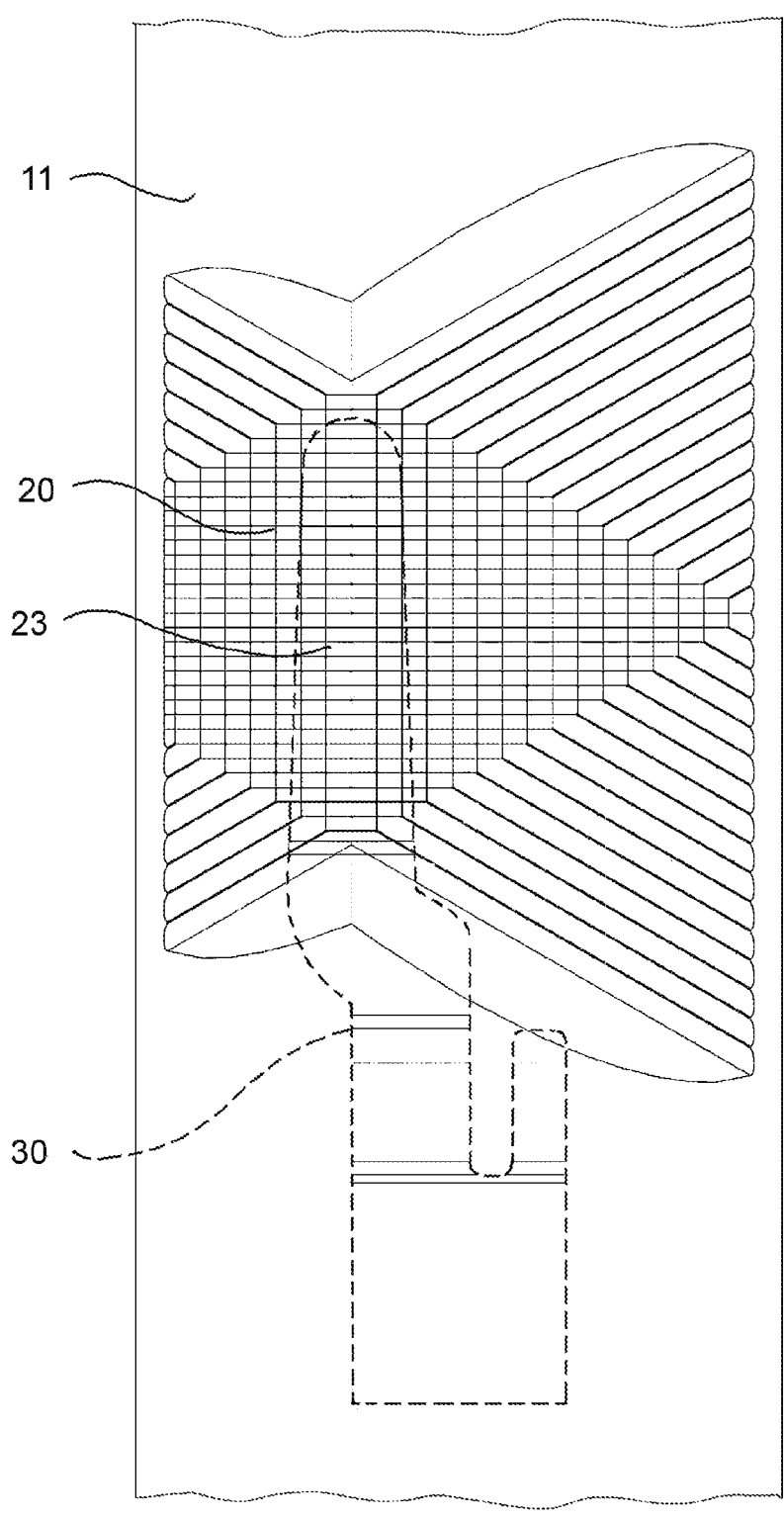
FIG. 9 shows a workpiece comprising a surface micro-topography, according to a possible operating mode, in which a dashed line shows the shape profile of a tip link of a surgical instrument comprising a gripping surface having a surface micro-topography, according to an embodiment.
Figure 10A:
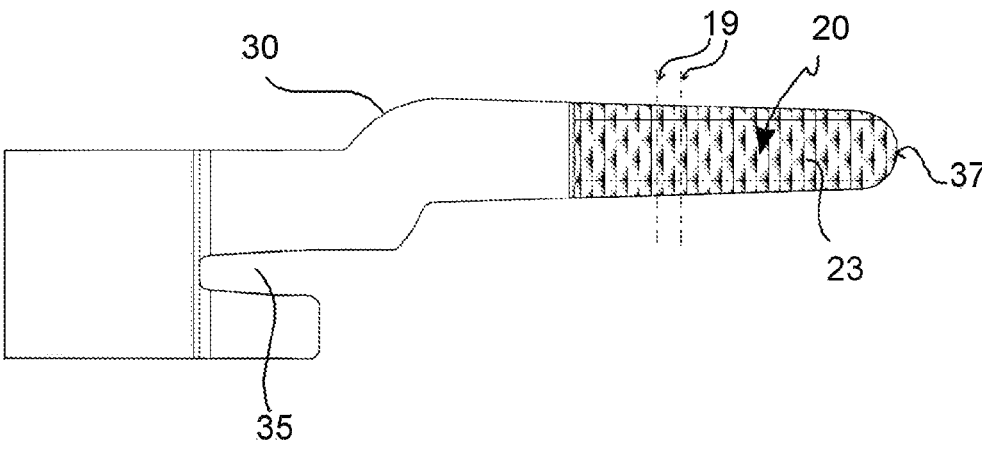
FIGS. 10-A and 10-B show a tip link having a gripping surface with surface micro-topography made in a single piece with the tip link body, according to an embodiment.
Figure 10B:
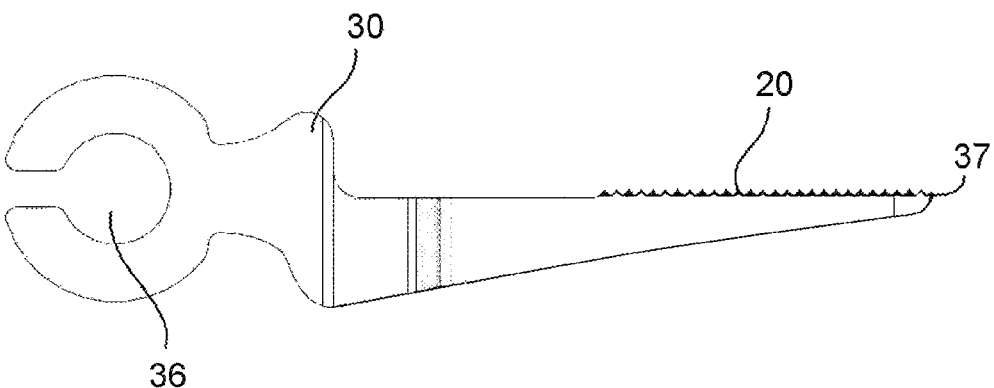
Figure 10C:
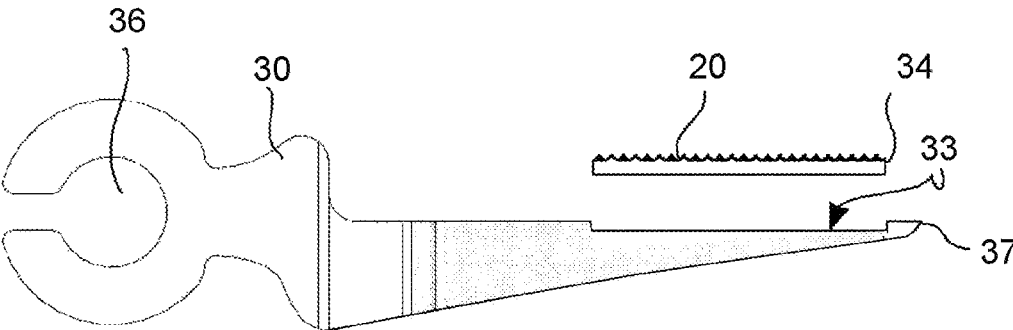

In accordance with a preferred embodiment, the shaping step makes at least one link 30 or 40 for a surgical instrument 1, said link 30 being provided with a gripping surface 23 comprising said surface micro-topography 20, as shown for example in FIG. 9.

In accordance with an embodiment, the shaping step makes at least one component 34 such as an insert, for example a "pad" or plate having said surface micro-topography 20 intended to be fixed to a surgical instrument 1 and/or a free end portion to be rigidly fixed to a gripping link. For example, said component 34 is intended to be welded or glued to the surgical instrument 1. For example, said component 34 can comprise a first face comprising said surface micro-topography 20 and a second opposite back face which can be ground and is intended to be fixed to a portion of a surgical instrument 1, for example it is intended to be fixed to a gripping portion of a surgical instrument 1 for example a gripping link, in which said surface micro-topography 20 forms a gripping surface 23 of the gripping link. The gripping surface 23 comprising the surface micro-topography 20 can be made in a separate piece with respect to the end effector and assembled thereto, and in accordance with an embodiment, a gripping link of an end effector comprises walls forming a fixing seat 33 in a single piece, and in which a component 34 or insert 34 (such as a pad, a plate, a block) comprising said surface micro-topography is fixed in said fixing seat 33 (for example by gluing, inter-locking, hooking, etc.).

In accordance with a possible operating mode, the shaping step comprises making two shaping through cuts. Said two shaping through cuts are preferably made on the workpiece 11 on two cutting planes orthogonal to each other. Said two shaping through cuts are preferably made on the workpiece 11 by means of the cutting wire 3 of the wire electro-erosion machine 2. Therefore, in accordance with this operating mode, at least four cuts are made on the workpiece 11 through the cutting wire 3, in which two cuts belong to the step of making the surface micro-topography 20 and two cuts belong to the shaping step.

Between said two shaping through cuts of the shaping step, the further step of rotating the workpiece 11 about a second shaping rotation axis, which is orthogonal to said rotation axis R-R, by an angle substantially equal to 90° can be included. Preferably, said second shaping rotation axis is coincident with or parallel to the longitudinal extension axis X-X of the at least one workpiece 11. This rotating step can be accomplished by rotating said support 24.

In accordance with a preferred operating mode, the shaping step is performed after the step of making a surface micro-topography. Between the step of making a surface micro-topography 20 and the shaping step, a further step of rotating the workpiece with respect to the cutting wire 3 about said rotation axis R-R can be included. Thereby, for example, it is possible to arrange the workpiece 11 aligned with the cutting wire 3 or orthogonal to the cutting wire 3 before the shaping step, where at the end of the second micro-texturing through cutting of the step of making a surface micro-topography 20, the workpiece 11 is inclined with respect to the cutting wire 3.

By virtue of such a method, replacements of the work-piece 11 between the micro-texturing through cuts of the step of making a surface micro-topography are avoided. An improved cutting accuracy suitable for extreme miniaturiza-tion is thus allowed, and a single initial calibration step is allowed if required.

By virtue of such a method, replacement or repositioning of the workpiece 11 on the support 24 between the shaping through cuts of the shaping step as well as between said shaping cuts and said micro-texturing cuts of the step of making a surface micro-topography is avoided. An improved cutting accuracy suitable for extreme miniaturiza-tion is thus allowed, and a single initial calibration step is allowed if required.

The shaping step can comprise the step of separating at least said surface micro-topography 20 from the support 24 of the workpiece 11. For example, the second shaping through cut obtains said separating step. In such a case, it is possible to include a further step of rotating the workpiece 11 with respect to the cutting wire 3 before the shaping step about a rotation axis which is parallel or coincident with the longitudinal extension axis X-X of the workpiece 11.

As mentioned above, the mounting step can comprise mounting the at least one workpiece 11 to a support 24 and the rotating step can comprise rotating said support 24 with respect to the cutting wire 3.

In accordance with a possible operating mode, the mount-ing step comprises: providing a tooling or jig which at least partially forms said support 24, and mounting the at least one workpiece 11 to the tooling, and mounting the tooling to the wire electro-erosion machine 2. For example, said tool-ing or jig can comprise opposite non-parallel positioning surfaces 31, 32 intended to form tooling positioning abutments on the wire electro-erosion machine 2 to position the at least one workpiece conveniently for performing the step of making said surface micro-topography 20. At least one further positioning abutment can be provided for positioning the at least one workpiece in a suitable manner for performing the shaping step. In accordance with an embodiment, said tooling or jig is foldable, and the rotating step is performed by rotating the tooling with respect to the cutting wire 3. The angle between the opposite positioning surfaces 31, 32 of the jig or tooling can be in relation to the rotation angle of the workpiece 11 between the through cuts of the step of making a surface micro-topography 20, and thus can be in relation to the angle between the reliefs 15 (or between the recesses 16) made with the first through cut and the reliefs 15 (and the recesses 16) made with the second through cut of the step of making a surface micro-topography 20. Therefore, the gauge of the resulting straight transverse through channels 19 may depend on the choice of the angle between the opposite positioning surfaces 31, 32 of the jig or tooling.

The tooling or jig of the support 24 can be operatively connected to one or more motors 25 for performing the rotation of the workpiece 11 about the rotation axis R-R of the step of making a surface micro-topography 20 and if required for performing the further rotation of the shaping step. For example, said one or more motors 25 rotate the support 24 comprising said tooling or jig.

In accordance with a possible operating mode, the mounting step comprises providing a robotic arm forming said support 24, and mounting the at least one workpiece to the robotic arm, as diagrammatically shown in FIG. 5. For example, said robotic arm can comprise a gripping terminal which directly or indirectly grasps said at least one workpiece 11, for example by interposing a grasping jig comprising a grasping portion. The term "grasp" here also means the embodiment in which the robotic arm is directly or indirectly fixed, for example screwed and/or coupled to the at least one workpiece, for example by interposing said grasping jig. In accordance with this operating mode, the rotating step is preferably performed by operating the robotic arm. The robotic arm can be provided with two or more axes (for example, it can be a "pitch-yaw" type robotic arm).

In accordance with a possible operating mode, the step of providing a wire electro-erosion machine 2 comprises providing the wire electro-erosion machine 2 with a positioning system for the workpiece 11 with at least one rotary axis (for example: a rotary spindle), at least partially forming said support 24 as diagrammatically shown in FIG. 4. In such a case, the rotating step can be performed by operating the rotary axis. Said positioning system for the workpiece 11 of the electro-erosion machine 2 can comprise at least two non-parallel rotary axes.

By virtue of the suggested solutions, it is possible to carry out a manufacturing process having the advantage of eliminating burrs and deburrs on the surface micro-topography 20, which at the same time is precise on the edges and sharp edges to facilitate the grip and increase the gripping capacity of the gripping surfaces of a surgical instrument 1.

By virtue of the suggested solutions, it is possible to carry out a manufacturing process for the removal of material capable of making very sharp edges with very high cutting precision and micro-texturing, making it adapted to make miniaturized gripping surfaces as well as miniaturized micro-texturing processes.

By virtue of the suggested solutions, it is possible to make gripping surfaces of a surgical instrument 1 adapted to grasp rigid objects in a predefinable orientation.

In accordance with a general embodiment, there is provided a surgical instrument 1 comprising at least one functional surface comprising a surface micro-topography 20.

The at least one functional surface can be a gripping surface 23.

The at least one functional surface can be a support surface, a positioning surface, etc.

The surface micro-topography is preferably made by wire electro-erosion, in accordance with any one of the operating modes described above.

Preferably, the surgical instrument 1 comprises two facing gripping surfaces 23, in which at least one, but also both, of the surface micro-topographies 20 of the gripping surfaces 23 are made by wire electro-erosion.

The gripping surfaces 23 are intended to jointly perform a gripping action on a surgical or microsurgical needle and/or a suture thread.

The surface micro-topography of one gripping surface 23 can be offset from the surface micro-topography of the other facing gripping surface 23.

Where the surface micro-topographies of the gripping surfaces 23 are both of the type having reliefs 15 and recesses 16 all parallel to each other with corresponding pitch or periodicity T1, T2 between the first and second gripping surfaces, then the reliefs 15 of one gripping surface 23 can be arranged offset with respect to the reliefs of the other gripping surface so that the reliefs of one gripping surface face one another and for example abut against the recesses 16 of the other gripping surface.

For example, said reliefs 15 made by the cutting wire 3 can be ridges or cusps extending along a substantially straight direction and parallel to the cutting wire 3 during the first through cut. For example, said recesses 16 made by the cutting wire 3 can be open channels with a curved bottom which extend substantially straight and parallel to the ridges or cusps of said reliefs 15 and thus parallel to the cutting wire 3 during the first through cut.

Where provided, the raised islands 17 of one gripping surface 23 are preferably offset with respect to the raised islands 17 of the other gripping surface 23 so that they are received in the grooves 18 of the latter when the gripping surfaces 23 are in a closing configuration.

In accordance with an embodiment, said surface micro-topography 20 can belong to only one portion of the gripping surface 23. For example, the surface micro-topography can be made only on a longitudinal band of the gripping surface behind a free end 37 of a link 30 of the end effector of the surgical instrument but which does not comprise such a free end 37. A first portion of the gripping surface 23 with the surface micro-topography 20 can be used to grasp a surgical or micro-surgical needle while a second portion 38 can be used to grasp a suture thread, separately or concurrently with grasping said needle.

By virtue of the sizing and location of the portions with locally different features on the gripping surface, it is possible to adapt the manufacturing based on the tissue or the device which the gripping surface will have to grasp when in operating conditions. For example, a portion with sharp edges similar to an indentation and/or punching can be dedicated to grasping a surgical needle and/or a biological tissue which is difficult to grasp, while a flat portion of the same gripping surface can be dedicated to grasping suture threads or biological tissues which are not damaged.

As mentioned above, in accordance with an embodiment, a surgical instrument 1 comprises two facing gripping surfaces 23,43 in which both gripping surfaces comprise a surface micro-topography 20 having reliefs 15 and recesses 16 all having a mainly transverse extension which are all parallel to each other. The pitch between adjacent reliefs can vary. The direction of the reliefs 15 and the recesses 16 can be transverse and preferably orthogonal to the longitudinal extension of the gripping surface 23.

Figure 16:
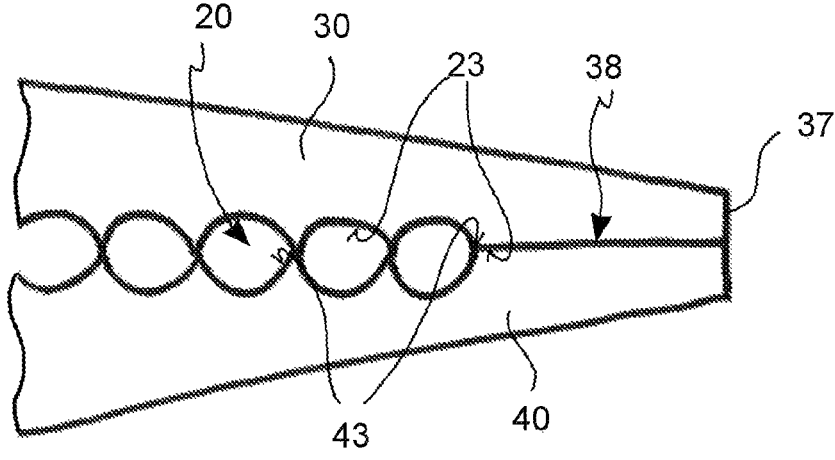
FIGS. 16 to 22 are diagrammatic views of a gripping surface of a surgical instrument, according to some embodiments.

As shown for example in FIG. 16, two facing gripping surfaces 23, 43 of respective gripping links 30, 40 of a surgical instrument 1 each comprise a surface micro-topography 20 having reliefs 15 and recesses 16, and all the reliefs and recesses of both gripping surfaces are all parallel to each other and oriented transversely (preferably orthogonal) to the longitudinal extension of the respective gripping link 30, 40, forming parallel ridges, in which the ridges formed by the reliefs 15 of one gripping surface 23 face and are intended to abut against the ridges formed by the reliefs 15 of the other gripping surface 43, and in which each gripping surface 23, 43 comprises a second unworked portion 38, in which said second unworked portion 38 is arranged distally to the surface micro-topography 20 in both gripping surfaces 23, 43, making an unworked distal gripping portion. In this example, the pitch between the ridges formed by the reliefs 15 can be constant or variable and is the same for the two gripping surfaces 23, 43.

Figure 17:
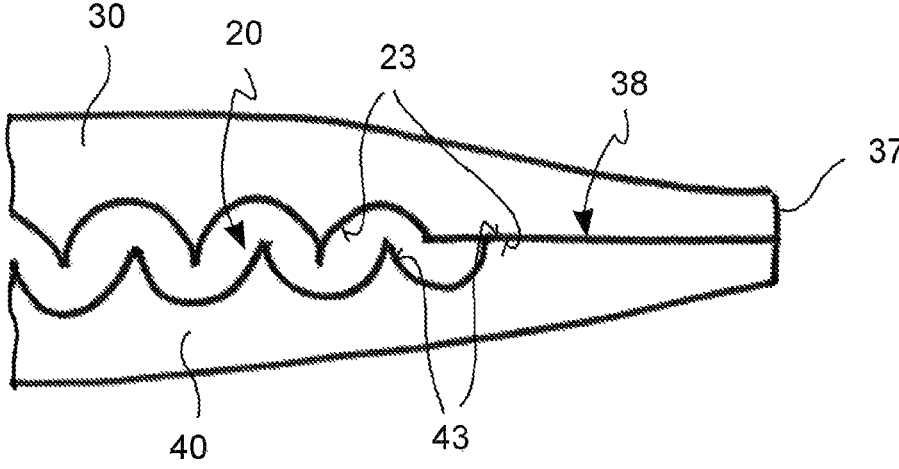

As shown for example in FIG. 17, two facing gripping surfaces 23, 43 of respective gripping links 30, 40 of a surgical instrument 1 each comprise a surface micro-topography 20 having reliefs 15 and recesses 16, and all the reliefs and recesses of both gripping surfaces are all parallel to each other and oriented transversely (preferably orthogonal) to the longitudinal extension of the respective gripping link 30, 40, forming parallel ridges, in which the ridges formed by the reliefs 15 of one gripping surface 23 or 43 face and are intended to abut against the bottom of the recesses 16 of the other gripping surface 43 or 23, and in which each gripping surface 23, 43 comprises a second unworked portion 38, in which said second unworked portion 38 is arranged distally to the surface micro-topography 20 in both gripping surfaces 23, 43, making an unworked distal gripping portion. In this example, the pitch between the ridges formed by the reliefs 15 can be constant or variable and is the same for the two gripping surfaces 23, 24. By virtue of such a solution, it is possible to make straight transverse through channels 19 having a smaller gauge than the gauge of the cutting wire 3 of the electro-erosion machine 2.

Figure 18:
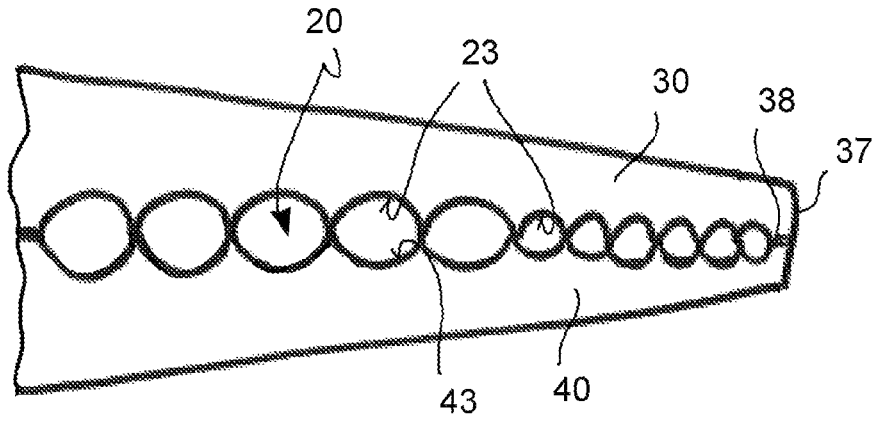

As shown for example in FIG. 18, two facing gripping surfaces 23, 43 of respective gripping links 30, 40 of a surgical instrument 1 each comprise a surface micro-topography 20 having 15 reliefs and recesses 16, and all the reliefs and recesses of both gripping surfaces are all parallel to each other and oriented transversely (preferably orthogonal) to the longitudinal extension of the respective gripping link 30, 40, forming parallel ridges, in which the ridges formed by the reliefs 15 of one gripping surface 23 face and are intended to abut against the ridges formed by the reliefs 15 of the other gripping surface 43. In this example, the pitch between the ridges formed by the reliefs 15 is variable but is the same for the two gripping surfaces 23, 43, and in particular the pitch between the reliefs 15 is reduced in a distal portion of the gripping surface 23, 43. A second unworked portion 38 can be provided close to the distal end 37.

Figure 19:
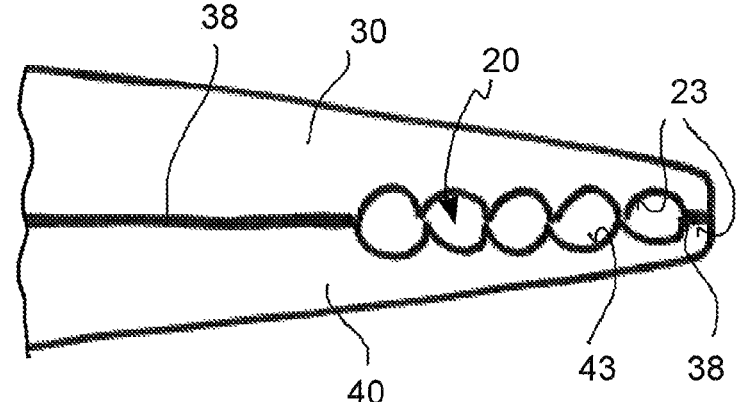

As shown for example in FIG. 19, two facing gripping surfaces 23, 43 of respective gripping links 30, 40 of a surgical instrument 1 each comprise a surface micro-topography 20 having reliefs 15 and recesses 16, and all the reliefs and recesses of both gripping surfaces are all parallel to one another and oriented transversely (preferably orthogonally) to the longitudinal extension of the respective gripping link 30, 40, forming parallel ridges, in which the ridges formed by the reliefs 15 of one gripping surface 23 face and are intended to abut against the ridges formed by the reliefs 15 of the other gripping surface 43. In this example, the pitch between the ridges formed by the reliefs 15 is constant and is the same for the two gripping surfaces 23, 43. A second unworked portion 38 can be provided close to the distal end 37. A second unworked portion 38 of the gripping surface 23, 43 placed proximally and adjacent to the surface micro-topography 20 can be provided.

Figure 20:
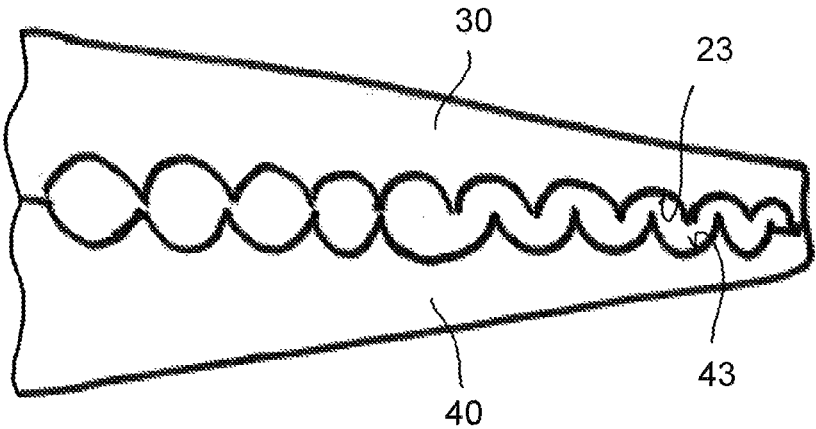

As shown for example in FIG. 20, two facing gripping surfaces 23, 43 of respective gripping links 30, 40 of a surgical instrument 1 each comprise a surface micro-topography 20 having reliefs 15 and recesses 16, and all the reliefs and recesses of both gripping surfaces are all parallel to each other and oriented transversely (preferably orthogonal) to the longitudinal extension of the respective gripping link 30, 40, forming parallel ridges, in which the ridges formed by the reliefs 15 of one gripping surface 23 face and are intended to abut against the bottom of the recesses 16 of the other gripping surface 43 or 23. In this example, the pitch between the ridges formed by the reliefs 15 is constant and is the same for the two gripping surfaces 23, 43. A second unworked portion 38 can be provided close to the distal end 37.

Figure 21:
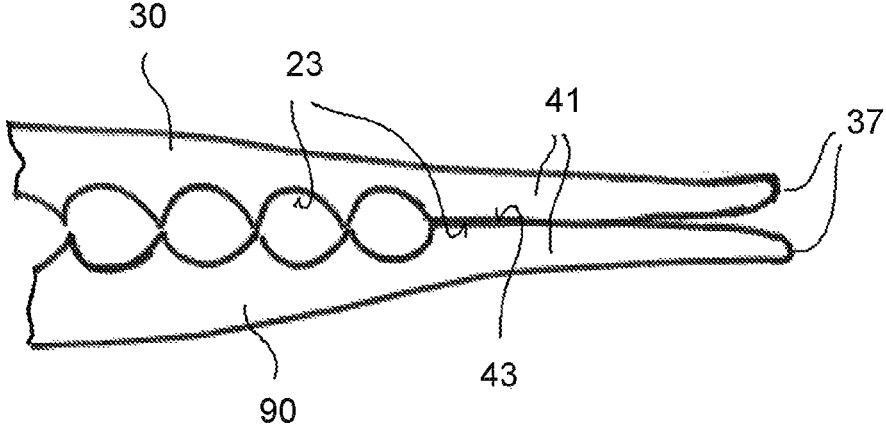

As shown for example in FIG. 21, two facing gripping surfaces 23, 43 of respective gripping links 30, 40 of a surgical instrument 1 each comprise a surface micro-topography 20 having reliefs 15 and recesses 16, and all the reliefs and recesses of both gripping surfaces are all parallel to one another and oriented transversely (preferably orthogonally) to the longitudinal extension of the respective gripping link 30, 40, forming parallel ridges, in which the ridges formed by the reliefs 15 of one gripping surface 23 face and are intended to abut against the ridges formed by the reliefs 15 of the other gripping surface 43, and in which close to the distal end 37 of the respective link 30, 40, the gripping surfaces 23,43 each further comprise an elastically flexible elastic element 41. The gripping surface 23, 43 at said elastic element 41 is preferably unworked, forming a second unworked portion 38 at the elastic element 41. The elastic element 41 can be an elastically flexible portion of a gripping link 30, 40 and/or a gripping surface 23, 43.

Figure 22:
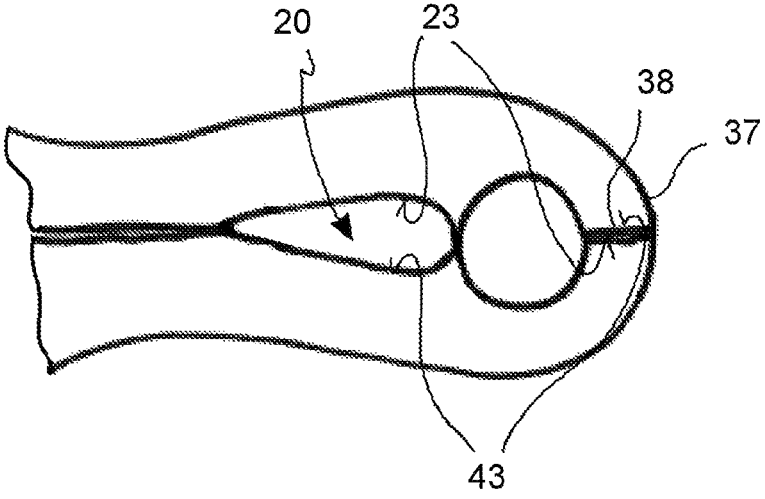

As shown for example in FIG. 22, two facing gripping surfaces 23, 43 of respective gripping links 30, 40 of a surgical instrument 1 each comprise a surface micro-topography 20 having reliefs 15 and recesses 16, and all the reliefs and recesses of both gripping surfaces are all parallel to each other and oriented transversely (preferably orthogonal) to the longitudinal extension of the respective gripping link 30, 40, forming parallel ridges, in which the ridges formed by the reliefs 15 of one gripping surface 23 face and are intended to abut against the ridges formed by the reliefs 15 of the other gripping surface 43, and in which close to the distal end 37 of the respective link 30, 40, the gripping surfaces 23,43 each further comprise a second unworked portion 38.

Figure 15A:
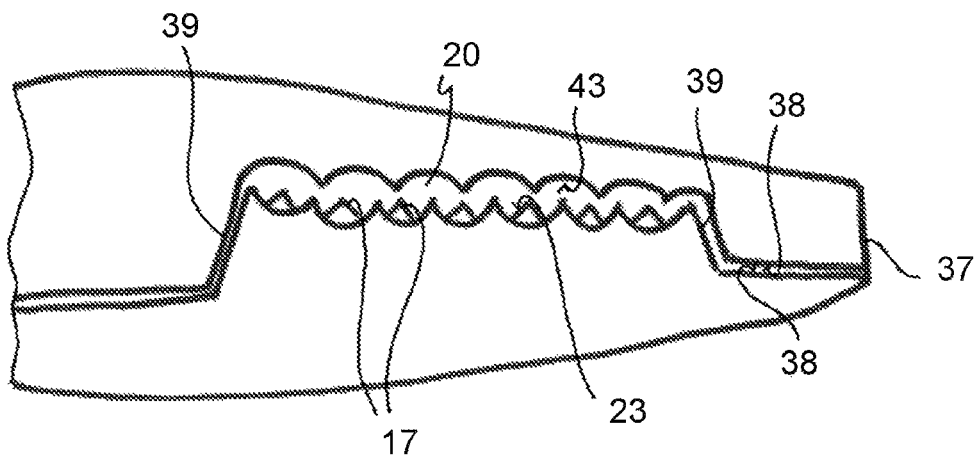
FIG. 15-A diagrammatically shows two gripping surfaces of a surgical instrument in a closing configuration, according to an embodiment.
Figure 15B:
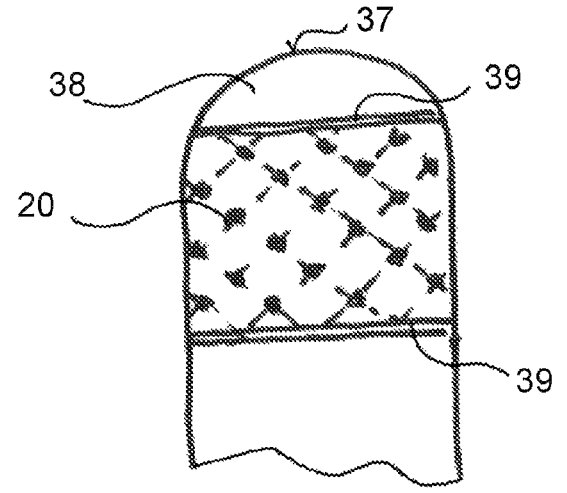

As mentioned above, in accordance with an embodiment, a surgical instrument 1 comprises two facing gripping surfaces 23,43 in which both gripping surfaces comprise a surface micro-topography 20 having reliefs 15 and recesses 16. In accordance with an embodiment, at least one surface micro-topography 20 (i.e., at least the surface micro-topography of the gripping surface 23 or gripping surface 43) comprises raised islands 17 delimited by grooves 18. As shown for example in FIG. 14, the raised islands 17 of one gripping surface 23 face and are received inside grooves 18 of the other gripping surface 43. In accordance with an embodiment, as shown for example in FIGS. 15A-B, said second portion 38 of the gripping surface 23 is arranged to be recessed with respect to the surface micro-topography 20 made, so that a step 39 is interposed between the second portion 38 and the surface micro-topography 20. Preferably, the step protrudes by an amount which is greater than the height of the peaks 12 with respect to the valleys 13 made by the at least one through cut.

Figure 15C:
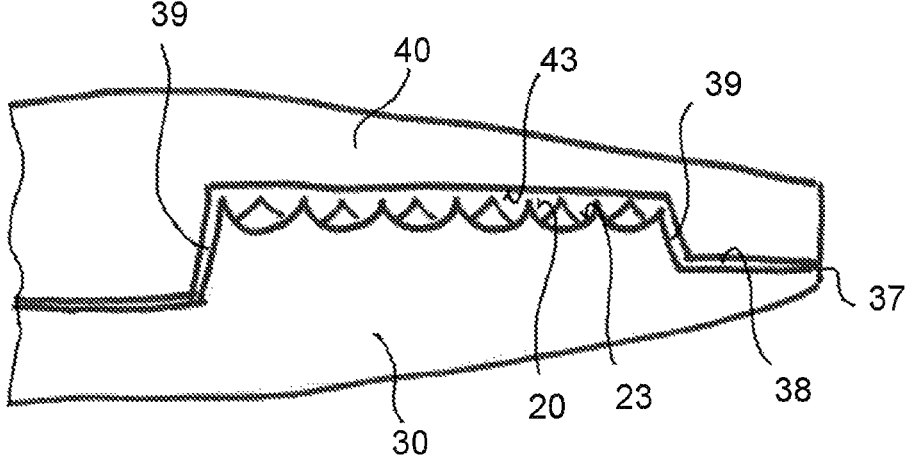

As mentioned above, in accordance with an embodiment, a surgical instrument 1 comprises two facing gripping surfaces 23,43 in only one of said gripping surfaces 23 comprises a surface micro-topography 20 having reliefs 15 and recesses 16 forming raised islands 17 delimited by grooves 18. As shown for example in FIG. 15-C, one gripping surface 23 comprises a surface micro-topography 20 having raised islands 17 delimited by grooves 18, and the other facing gripping surface 43 is substantially flat i.e., substantially unworked i.e., does not comprise a controlled surface micro-topography 20.

In accordance with an embodiment, the end effector 29 of the surgical instrument 1 is an end effector 29 of the articulated cuff type, comprising at least the degree of freedom of opening/closing (or grip) G between two gripping links 30, 40 each comprising a gripping surface 23, 43. The end effector 20 is preferably positioned at the distal end of a stick 42 or rod 42 or shaft 42 extending from a transmission interface portion 44 of the surgical instrument 1 at the end effector 29. The end effector 29 preferably comprises a plurality of links comprising said two gripping links 30, 40 articulated together defining the degree of freedom of opening/closing G, and a support link 45 (or clevis link 45) having two prongs 46, in which the two gripping links 30, 40 are both articulated to the prongs 46 of the support link 45 defining a degree of freedom of yaw Y between the support link and each or both of the gripping links 30, 40. The gripping links 30, 40 preferably each comprise a free end 37. A further connecting link 47 to the shaft 42 can be provided, which can be fixed to the distal end of the shaft 42 by means of the pins 52 and articulated to the support link 45 defining a degree of freedom of pitch P. A further degree of freedom of roll R of the end effector 29 can be present about the longitudinal axis of the shaft 42. As shown for example in FIG. 23, actuation tendons 48, 49, 50, 51 are connected to the links of the end effector 29 to activate the degrees of freedom. Preferably a pair of antagonistic tendons is connected to each link. In the example shown, the gripping link 40 is moved in opposite directions about the yaw axis Y-Y by the pair of tendons 48, 49, and in which the tendon 51 moves the other gripping link 30 about the yaw axis Y-Y, while the tendon 50 moves the support link 45 about the pitch axis P-P.

Figure 23:
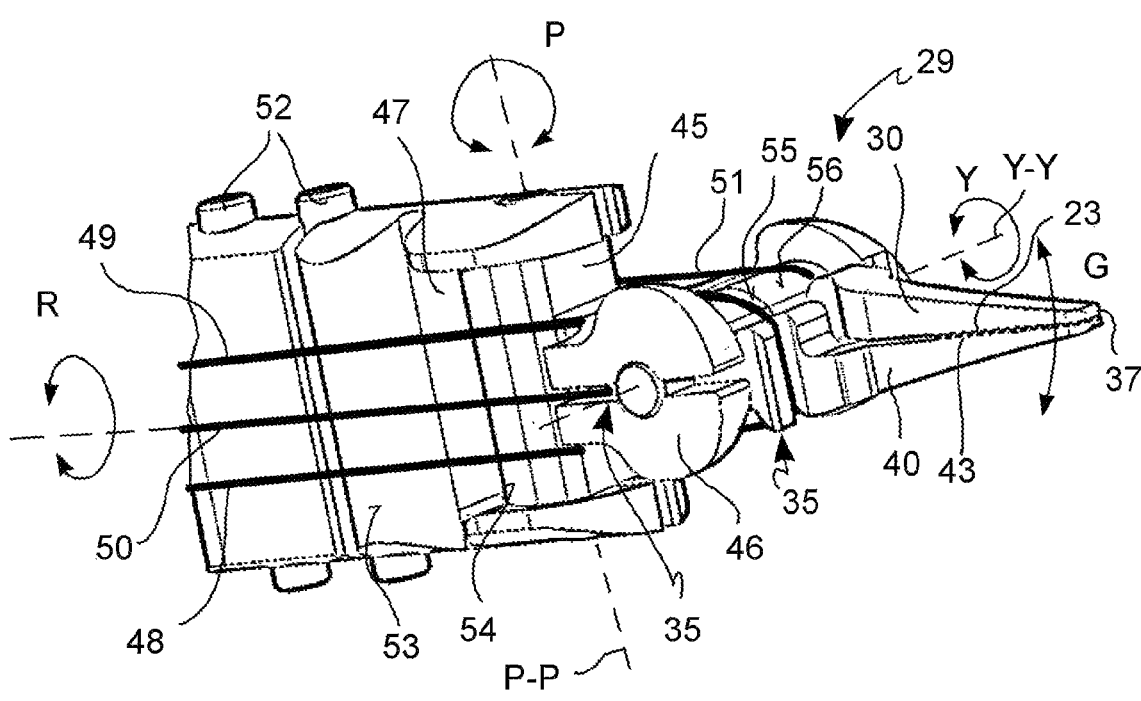
FIG. 23 is an axonometric view of an end effector of a surgical instrument in a closing configuration of the degree of freedom of opening/closing, according to an embodiment, in which certain parts (such as the shaft or rod) are omitted for clarity.
Figure 24:
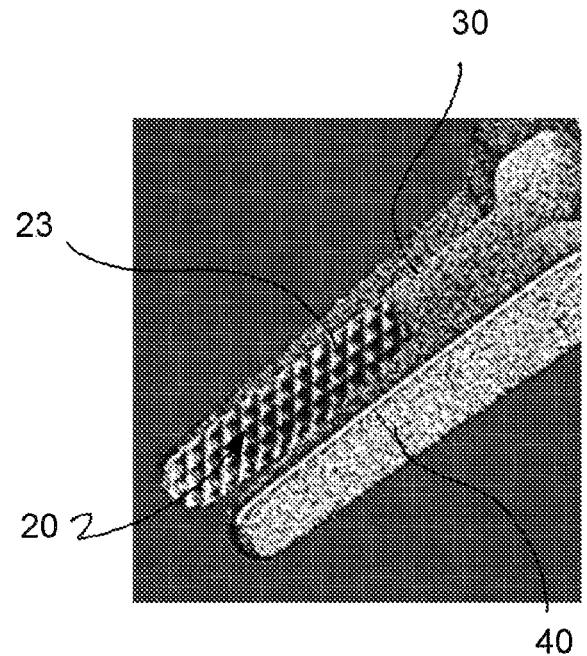
FIG. 24 is a microscope photographic image showing a gripping surface having a surface micro-topography, according to an embodiment.
Figure 25A:
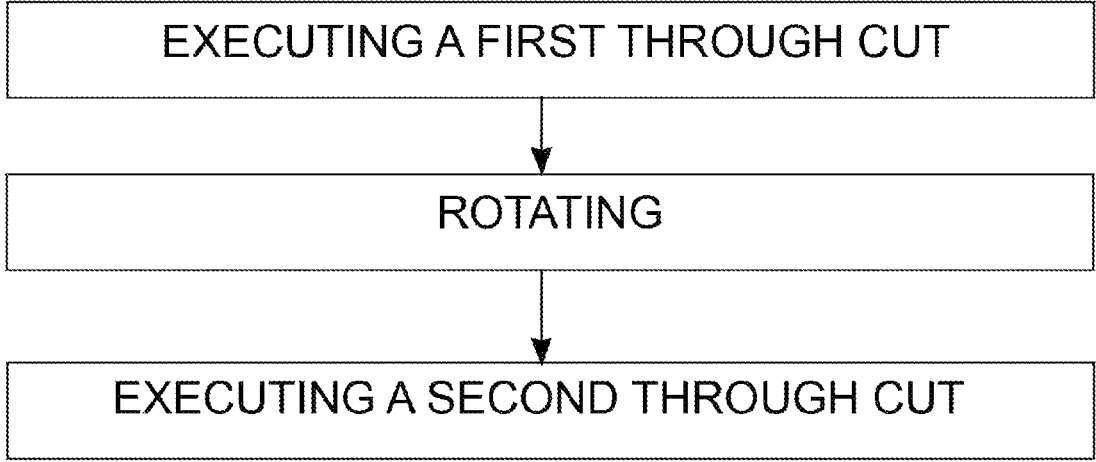
FIG. 25-A shows a block diagram of a method, according to a possible operating mode.
Figure 25B:
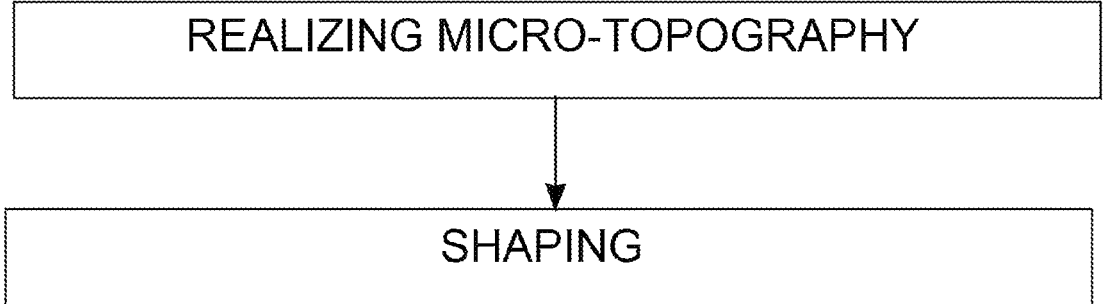
Figure 25C:
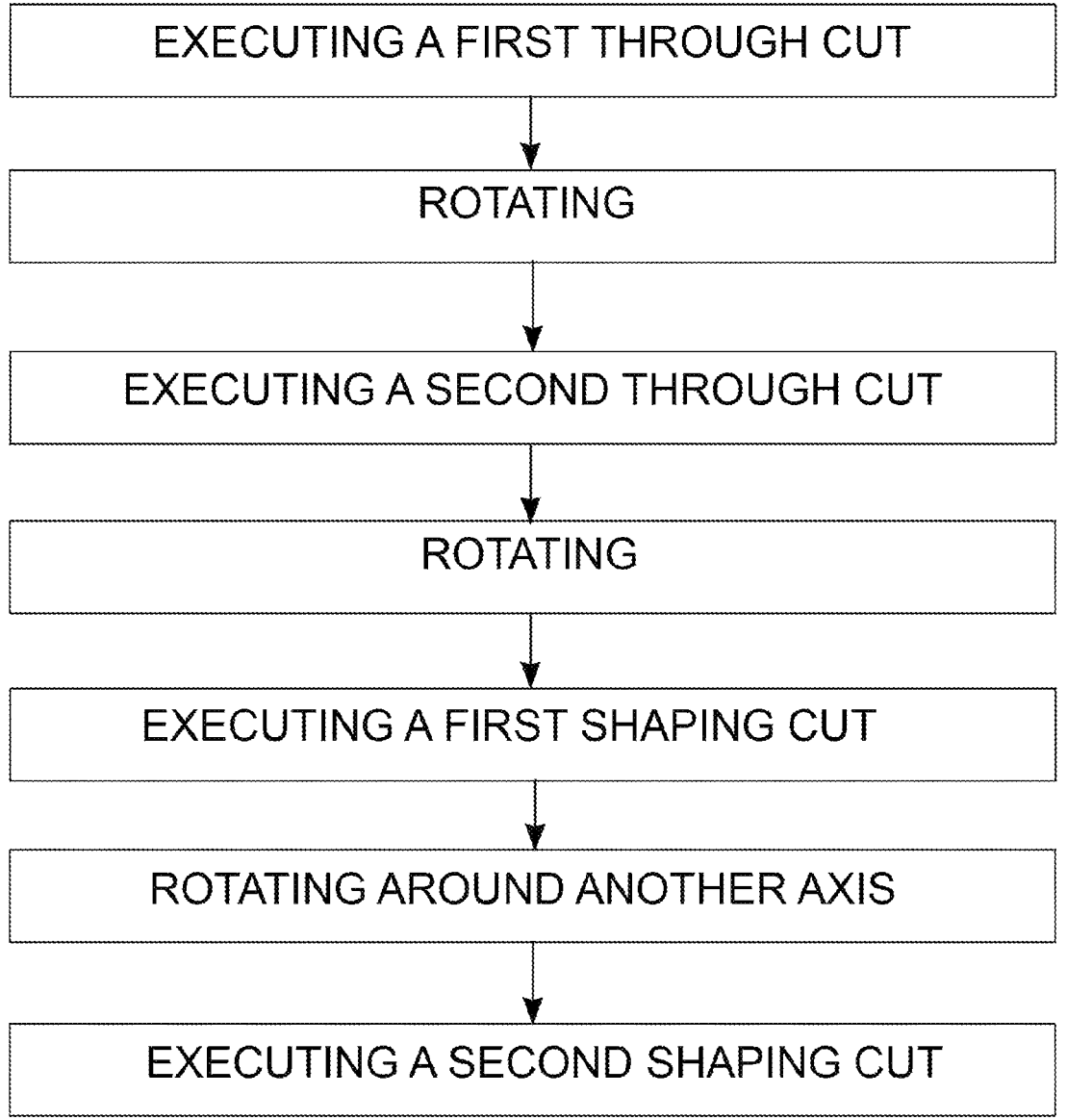

In accordance with a preferred embodiment, as shown for example in FIG. 23, the links of the end effector 29 lack channels for guiding the actuation tendons. In accordance with a preferred embodiment, the links of the end effector 29 comprise convex ribbed surfaces 53, 54, 55 in contact with the actuation tendons. The convex ribbed surface 53 is parallel to the pitch axis P-P and belongs to the connecting link 47 and all the tendons 48, 49, 50 in contact therewith are configured to slide on the convex ribbed surface 53 during the movement of the degrees of freedom of pitch, yaw and opening/closing P, Y, G. The convex ribbed surface 54 belongs to the support link 45, and the tendons 48, 49 for moving the gripping link 40 are intended to slide on the convex ribbed surface 54 during the actuation of the degree of freedom of opening/closing G, while the tendon 50 for moving the support link 45 does not slide on the convex ribbed surface 54 (but is limited to winding/unwinding). The convex ribbed surface 55 is parallel to the yaw axis Y-Y and belongs to the gripping link 40, and the tendons 48, 49 for moving the gripping link 40 about the yaw axis Y-Y do not slide on said convex ribbed surface 55. The convex ribbed surface 56 is parallel to the yaw axis Y-Y and belongs to the gripping link 30, and the tendons 51 for moving the gripping link 30 about the yaw axis Y-Y do not slide on said convex ribbed surface 56.

The actuation tendons are preferably received at respective termination sites 35 provided on the links to be actuated.

Each link can be made in a single piece.

In accordance with an embodiment, each link of the end effector 29 is made by wire electro-erosion shaping (WEDM) with a wire electro-erosion machine 2. For example, the above-described shaping step can make said gripping links 30, 40 each comprising a convex ribbed surface 55, 56.

In accordance with a general embodiment, there is provided a robotic surgery system 100, comprising at least one surgical instrument 1 according to any one of the embodiments described above. The robotic surgery system 100 can further comprise at least one robotic manipulator 101 for moving at least the end effector 29 of the surgical instrument 1 under the control of at least one master control device 102. The master control device 102 can be mechanically ungrounded and associated with a tracking system.

In accordance with a general embodiment, there is provided a wire electro-erosion apparatus, comprising a wire electro-erosion machine 2 comprising a cutting wire 3 according to any one of the previously described embodiments, and a support 24 for supporting at least one workpiece 11 in at least one predeterminable orientation of the workpiece 11 with respect to the cutting wire 3.

The support 24 is preferably a support according to any one of the previously described embodiments.

As mentioned above, the surface micro-topography 20 having raised islands 17 delimited by grooves, is made by a wire electro-erosion cut method. This allows to obtain a very high cutting precision and allows to realize pointed tips, and/or ridges and/or sharp edges with a very high positioning certainty. In addition, it is possible to obtain a very high density of presence of raised islands 17, preferably all pointed. In addition, it is possible to obtain these raised islands 17 which are particularly slender, i.e. high, with respect to the level of the grooves that surround them, without making them too fragile.

According to an embodiment, the surface micro-topography 20 presents said plurality of raised islands 17 which are arranged with a density comprised in the range of 50-300 raised islands 17 per square millimeter.

According to an embodiment, a plurality of said of raised islands 17, and preferably all of them, have a pointed free end (cusp) having a tip angle less than 60°, for example equal to about 45°, and preferably of about 30°.

Thanks to the use of such a manufacturing method by wire electro-erosion, a three-dimensional surface micro-topography 20 is obtained which is particularly suitable to be miniaturized, to form a gripping surface suitable for firmly grasping a surgical micro-needle.

The use of such a manufacturing method by wire electro-erosion, also allows to realize this surface micro-topography 20 by material removal, avoiding to provide heat treatments on the material. In accordance with an embodiment, the material is processed by making the surface micro-topography 20 starting from a martensitic steel block, which has a better mechanical strength than austenitic steel, and therefore is particularly desirable at the micro-scale, without never impose a phase transition towards the austenitic phase.

The raised islands 17, where they are made by means of said two cuts, present two pairs of opposite faces 57, 58, and in accordance with an embodiment, said two pairs of opposite faces 57, 58 which join together forming a pointed end, like a pyramid, and at the joint of two adjacent faces is formed a sharp edge 59. In other words, two pairs of opposite faces 57, 58 form the leading edges of each raised island 17, and a sharp ridge is formed between two adjacent faces of each raised island 17. At the joint of the ridges, the pointed end of the raised island 17 is formed. In accordance with an embodiment, the raised islands 17 each comprise two pairs of opposite faces 57; 58 which join forming, between adjacent faces 57, 58 of said two pairs of opposite faces, a ridge sharp edge 59.

The ridge sharp edge 59 is preferably concave. In other words, the cutting wire forms opposite concave faces 57, 58 which join in a ridge sharp edge 59 which is concave. This makes it possible to make the raised island 17 with a pointed end 28 more slender.

Being made by wire electro-erosion, the base of the raised island 17 (i.e. at the level of the grooves) can be a quadrangular base, for example rhomboid, rectangular or square, and the shape of the base may depend on the choice of angle α.

It is therefore possible to obtain a micro-texturing, that is a three-dimensional micro-topography, which allows a better ability to grip objects to be grasped such as a surgical needle.

The fact that the ridges and the end of the raised island are sharp, i.e. pointed, is desirable because it favors a firm grip. The tip angle of the ridges is preferably less than 60°, for example equal to about 45°, and/or about 30°. Preferably, the tip angle belongs to the range of 30°-60°.

Preferably, each face of the raised island 17, being made with the cutting wire by wire electro-erosion, is a ribbed surface with rectilinear generatrices all parallel to each other, and even more preferably the opposite faces of each pair of faces are surfaces ruled with rectilinear generatrices all parallel to each other.

Each face of the raised island 17 can be a curved face, that is a concave ribbed surface with rectilinear generatrices all parallel to each other.

The rectilinear generatrices of the ruled surfaces forming two adjacent faces can form an angle between them equal to the angle α.

According to an embodiment, the gripping surface 23 comprises a density of 60-240 raised islands 17 per square millimeter. The density can be variable in different portions of the gripping surface 23.

By virtue of the features described above, provided either separately or in combination in particular embodiments as well as in particular operating modes, it is possible to provide a solution to the aforementioned needs, achieving the aforesaid advantages, and in particular:

an extreme miniaturization of microsurgical practices as well as surgical instruments is supported;

it is possible to firmly grasp needles of very small gauge, up to 12/0;

for example, miniaturized surgical needle means a needle size less than or equal to 8/0 (about 150 µm) as well as less than or equal to 12/0 (about 50 µm), while miniaturized suture thread means a suture thread having a diameter less than 50 µm (e.g. less than or equal to 30 µm);

it is possible to make a miniaturized, robust surgical end effector with improved gripping capabilities on needles and/or suture threads and/or miniaturized anatomical districts;

it is possible to make a miniature surgical end effector provided with gripping surfaces having a surface micro-topography made with a manufacturing method by wire electro-erosion, with multiple passes of the cutting wire (for example at least 5 passes), which thus eliminates and prevents thermal stresses during the process itself such as to alter the crystalline lattice of the workpiece and therefore makes the process adapted to make the surface micro-topography on the same piece which will form a gripping link of the miniaturized surgical end effector;

the formation of burrs and deburrs is avoided and a highly precise manufacturing process is provided for making miniaturized sharp edges with the aim of increasing the gripping capacity;

the surgical instrument of improved gripping capacities is provided;

it is possible, for example, to predetermine the desired gripping orientation of a surgical or microsurgical needle by virtue of the distribution of said reliefs and recesses;

a manufacturing process which is repeatable and at the same time versatile and applicable to a variety of clinical and in particular surgical areas is provided;

the functional surface which is subjected to the surface micro-topography process could be a functional surface which does not necessarily contribute to a gripping action.

In order to meet specific, contingent needs, those skilled in the art can make several changes and adaptations to the above-described embodiments and can replace elements with other functionally equivalent ones, without departing from the scope of the appended claims.

| LIST OF REFERENCE SIGNS | |
| --- | --- |
| 1 | Surgical instrument |
| 2 | Wire electro-erosion machine |
| 3 | Cutting wire |
| 4 | Machine head |
| 5 | Machine head |
| 6 | Roller or winding coil for the cutting wire |
| 7 | Tank |
| 8 | Hydraulic duct |
| 9 | Pump |
| 10 | Nozzle |
| 11 | Workpiece |
| 12 | Peak |
| 13 | Valley |
| 14 | Exposed portion |
| 15 | Relief |
| 16 | Recess |
| 17 | Raised island |
| 18 | Groove |
| 19 | Straight transverse channel |
| 20 | Surface micro-topography |
| 21 | Cutting path, or first cutting path of the first cut |
| 22 | Second cutting path of the second cut |
| 23 | Gripping surface of the surgical instrument |
| 24 | Support for the workpiece |

-continued

LIST OF REFERENCE SIGNS

| | |
|---|---|
| 25 | Motor |
| 26 | Extra ring-shaped cutting path |
| 27 | Edge level |
| 28 | Free end of raised island |
| 29 | Articulated end of the surgical instrument, or end effector |
| 30 | Link, or gripping link, of the end effector of the surgical instrument |
| 31, 32 | Tooling positioning surface |
| 33 | Fixing seat |
| 34 | Component or insert |
| 35 | Termination for a link tendon |
| 36 | Joint junction portion |
| 37 | Link free end |
| 38 | Second gripping surface portion |
| 39 | Step |
| 40 | Second link, or second gripping link of the end effector of the surgical instrument |
| 41 | Elastic element |
| 42 | Surgical instrument stick or rod or shaft |
| 43 | Second gripping surface |
| 44 | Surgical instrument transmission interface |
| 45 | Support link |
| 46 | Prong |
| 47 | Connecting link |
| 48, 49 | Pair of antagonistic tendons for gripping link actuation |
| 50 | Support link actuation tendon |
| 51 | Actuation tendon of the other gripping link |
| 52 | Shaft fixing pins |
| 53 | Convex ribbed surface of the connecting link |
| 54 | Convex ribbed surface of the support link |
| 55, 56 | Convex ribbed surface of the gripping link |
| 57, 58 | Opposite faces of the raised island |
| 59 | Ridge or sharp edge of the raised island |
| 100 | Robotic surgery system |
| 101 | Slave robotic manipulator |
| 102 | Master control device |
| R | Degree of freedom of roll |
| P | Degree of freedom of pitch |
| Y | Degree of freedom of yaw |
| G | Degree of freedom of opening/closing or grip |
| X-X | Longitudinal direction of the workpiece |
| R-R | Rotation axis |
| α | Rotation angle |
| W | Cutting wire feeding direction |
| UM | Cutting path modular unit |
| T1, T2 | Modular cutting path frequency or pitch |

The invention claimed is:

1. A method of manufacturing a gripping surface for an end effector of a surgical instrument by wire electro-erosion, comprising the following steps of:

providing a wire electro-erosion machine having a cutting wire;

mounting at least one workpiece to the wire electro-erosion machine;

making a surface micro-topography by wire electro-erosion;

wherein the step of making a surface micro-topography comprises the steps of:

performing a first through cut on the at least one workpiece according to a first cutting path comprising peaks and valleys, exposing at least one exposed portion on the at least one workpiece comprising reliefs and recesses corresponding to said peaks and valleys of the first cutting path;

then, rotating the at least one workpiece with respect to the cutting wire about a rotation axis;

then, performing a second through cut on the same at least one exposed portion of the workpiece according to a second cutting path comprising peaks and valleys, making on said at least one exposed portion a surface micro-topography having a plurality of raised islands delimited by grooves.

2. The method according to claim 1, wherein the surface micro-topography made has straight transverse passage channels, which are narrower, in at least one definable transverse direction, than a gauge of the cutting wire of the wire electro-erosion machine.

3. The method according to claim 1, comprising the further step of shaping the at least one workpiece, making at least one gripping link for a surgical instrument comprising said gripping surface having said surface micro-topography in a single piece.

4. The method according to claim 1, comprising the further step of shaping the at least one workpiece, making at least one component to be fixed to a link for a surgical instrument to make a gripping link for a surgical instrument comprising said gripping surface having said surface micro-topography; and/or wherein the method comprises the further step of fixing said at least one component to a fixing seat of the body of said gripping link.

5. The method according to claim 3, wherein the shaping step comprises making two shaping through cuts on two cutting planes.

6. The method according to claim 3, wherein the shaping step is performed after the step of making a surface micro-topography; and/or wherein between the step of making a surface micro-topography and the shaping step, the further step of rotating the workpiece with respect to the cutting wire about said rotation axis is performed.

7. The method according to claim 1, wherein said rotation axis extends parallel to a direction exiting from the exposed portion of the workpiece; and/or wherein said rotation axis extends orthogonal to extension of the cutting wire and orthogonal to a longitudinal extension direction of the at least one workpiece.

8. The method according to claim 1, wherein the rotating step comprises rotating the at least one workpiece with respect to the cutting wire by an angle greater than 45°.

9. The method according to claim 1, wherein:

the mounting step comprises providing a tooling and mounting the at least one workpiece to the tooling and the tooling to the wire electro-erosion machine; or wherein:

the mounting step comprises providing a robotic arm and mounting the at least one workpiece to the robotic arm; or wherein:

the step of providing a wire electro-erosion machine comprises providing the wire electro-erosion machine with a positioning system for the workpiece having at least one rotary axis.

10. The method according to claim 1, wherein the method comprises the further step of making an initial roughening on the workpiece, exposing a substantially flat surface to be worked on the workpiece;

and wherein the step of making an initial roughening is performed before the step of making a surface micro-topography.

11. The method according to claim 1, wherein at least one cutting path between said first and second cutting paths comprises a path modular unit, which includes at least one peak and at least one valley, wherein the path modular unit repeats with a certain periodicity.

12. The method according to claim 1, wherein the method makes two gripping surfaces configured to be coupled to each other when in operating conditions to perform a gripping action.

13. The method according to claim 1, wherein the material is processed by making the surface micro-topography starting from a martensitic steel block, avoiding imposing a phase transition towards an austenitic phase during phases of the method.

14. The method according to claim 3, wherein the shaping step comprises making two shaping through cuts on two cutting planes orthogonal to each other.

15. The method according to claim 1, wherein:

the mounting step comprises providing a tooling and mounting the at least one workpiece to the tooling and the tooling to the wire electro-erosion machine;

or wherein:

the mounting step comprises providing a robotic arm and mounting the at least one workpiece to the robotic arm; and wherein the rotating step is performed by operating the robotic arm;

or wherein:

the step of providing a wire electro-erosion machine comprises providing the wire electro-erosion machine with a positioning system for the workpiece having at least one rotary axis.

16. The method according to claim 1, wherein the method comprises the further step of making an initial roughening comprising an at least partial flattening, on the workpiece, and exposing a substantially flat surface to be worked on the workpiece;

and wherein the step of making an initial roughening is performed before the step of making a surface micro-topography.

* * * * *